United States Patent
Mohamed Ibrahim

(10) Patent No.: US 11,376,306 B2
(45) Date of Patent: Jul. 5, 2022

(54) PEPTIDES AND USES THEREFOR AS ANTIVIRAL AGENTS

(71) Applicant: Viramatix Sdn Bhd, Kuala Lumpur (MY)

(72) Inventor: Mohamed Rajik Mohamed Ibrahim, Kuala Lumpur (MY)

(73) Assignee: VIRAMATIX SDN BHD, Kuala Lumpur (MY)

( * ) Notice: Subject to any disclaimer, the term of this patent is extended or adjusted under 35 U.S.C. 154(b) by 0 days.

(21) Appl. No.: 16/613,382

(22) PCT Filed: May 26, 2017

(86) PCT No.: PCT/MY2017/050021
§ 371 (c)(1),
(2) Date: Nov. 13, 2019

(87) PCT Pub. No.: WO2018/217075
PCT Pub. Date: Nov. 29, 2018

(65) Prior Publication Data
US 2020/0113967 A1    Apr. 16, 2020

(51) Int. Cl.
*A61K 38/08* (2019.01)
*A61P 31/22* (2006.01)
*A61P 31/20* (2006.01)
*A61P 31/14* (2006.01)
*A61P 31/18* (2006.01)
*A61K 38/12* (2006.01)

(52) U.S. Cl.
CPC .............. *A61K 38/08* (2013.01); *A61K 38/12* (2013.01); *A61P 31/14* (2018.01); *A61P 31/18* (2018.01); *A61P 31/20* (2018.01); *A61P 31/22* (2018.01)

(58) Field of Classification Search
None
See application file for complete search history.

(56) References Cited

U.S. PATENT DOCUMENTS

| 10,538,554 B2 * | 1/2020 | Mohamed Ibrahim .. C07K 7/64 |
| 2013/0190228 A1 | 7/2013 | Schultz-Cherry |
| 2013/0205416 A1 | 8/2013 | Nash |

FOREIGN PATENT DOCUMENTS

| WO | 2001057072 | 8/2001 |
|----|------------|--------|
| WO | 2002077189 | 10/2002 |
| WO | 2003086326 | 10/2003 |
| WO | 2005105831 | 11/2005 |
| WO | 2006128294 | 12/2006 |
| WO | 2007041487 | 4/2007 |
| WO | 2009040529 | 4/2009 |
| WO | WO 2009/040529 | * 4/2009 |
| WO | 2009151313 | 12/2009 |
| WO | 2009152519 | 12/2009 |
| WO | WO 2010/037397 | * 4/2010 |
| WO | 2010099556 | 9/2010 |
| WO | 2012013979 | 2/2012 |
| WO | 2013040142 | 3/2013 |
| WO | WO 2013/040142 | * 3/2013 |
| WO | 2014210454 | 12/2014 |
| WO | 2016007751 | 1/2016 |
| WO | 2017090010 | 6/2017 |
| WO | 2018217075 | 11/2018 |

OTHER PUBLICATIONS

PCT Search Report prepared for PCT/IB2016/057146, dated Feb. 27, 2017.
Jaishankar, D., et al., "Characterisation of Proteolytically Stable D-Peptide That Surpresses Herpes Simplex Virus 1 Infection: Implications for the Development of Entry-Based Antiviral Therapy", Journal of Virology, 2015, 89(3), 1932-8.
Rajik, M., Jahanshiri, F., Omar, A. R., Ideris, A., Hassan, S. S., & Yusoff, K. (2009). Identification and characterisation of a novel anti-viral peptide against avian influenza virus H9N2. Virology journal, 6(1), 74.
Ben-Yedidia, T., Beignon, A. S., Partidos, C. D., Muller, S., & Arnon, R. (2002). A retro-inverso peptide analogue of influenza virus hemagglutinin B-cell epitope 91-108 induces a strong mucosal and systemic immune response and confers protection in mice after intranasal immunization. Molecular immunology, 39(5-6), 323-331.
Nair, D. T., Kaur, K. J., Singh, K., Mukherjee, P., Rajagopal, D., George, A., . . . & Salunke, D. M. (2003). Mimicry of native peptide antigens by the corresponding retro-inverso analogs is dependent on their intrinsic structure and interaction propensities. The Journal of Immunology, 170(3), 1362-1373.
Zhong, Y., Cai, J., Zhang, C., Xing, X., Qin, E., He, J., . . . & Song, H. (2011). Mimotopes selected with neutralizing antibodies against multiple subtypes of influenza A. Virology journal, 8(1), 542.
Internatioanl Search Report prepared for PCT/MY2017/050021, dated Sep. 7, 2017.

* cited by examiner

*Primary Examiner* — Sergio Coffa
(74) *Attorney, Agent, or Firm* — Brannon Sowers & Cracraft PC

(57) ABSTRACT

Peptides with anti-viral properties are disclosed herein. The peptides include dextro (D) or a mixture of dextro/levo (L)-amino acids, possess anti-viral properties against multiple types of enveloped viruses and matrix protein layer viruses and are useful as pharmaceutical compositions for the treatment or prevention of enveloped virus and matrix protein layer virus infections.

19 Claims, 8 Drawing Sheets

PEPTIDES AND USES THEREFOR AS ANTIVIRAL AGENTS

CROSS-REFERENCE TO RELATED APPLICATION

This application is a U.S. national entry application under 37 C.F.R. § 371(b) of International Application Serial No. PCT/MY2017/050021 filed May 26, 2017, the disclosure of which is incorporated herein by reference in its entirety.

TECHNICAL FIELD

This invention relates to therapeutic peptides which possess broad spectrum anti-viral activity against a wide variety of enveloped viruses and matrix protein layer viruses.

BACKGROUND

Viral infection by enveloped viruses and matrix protein layer viruses remains a profound problem for humankind. Though influenza viruses have attracted the attention of many researchers, viral treatments for the other enveloped viruses and matrix protein layer viruses, including but not limited to Herpes simplex virus, Cytomegalovirus, Respiratory Syncytial virus, and Human immunodeficiency viruses, remains a profound unmet medical need.

Respiratory syncytial viruses (RSV) belong to the family of Paramyxoviridae which contains enveloped, negative-sense, single-stranded and non-RNA genomes.[1] Though RSVs are one of the important paediatric pathogens, they can affect individuals of all ages, especially elderly and immuno-compromised individuals. RSVs infect only humans and are highly contagious. Currently there is no approved therapeutics available for treatment.[2] It is estimated that ~34 million children of <5 years of age are infected globally every year, resulting in ~4 million hospital admissions and 100,000-200,000 deaths. Generally, RSVs causes upper respiratory tract infections but 20-30% of infected children show symptoms of lower respiratory tract infections, such as bronchiolitis and/or pneumonia.[2] The symptoms of RSV infection include weakness, irritability, cough, wheezing, crackles, tachypnea and poor appetite. Factors such as heart diseases, chronic lung disease of prematurity, immunodeficiency and immuno-suppression can increase and worsen the symptoms of the disease. Current RSV infection therapies are mainly prescribed for prophylactic use in patients at high-risk or very high-risk situation.[3] A more general therapy, as well as a post-infection therapy, is needed.

Cytomegalovirus (CMV) belongs to the family of Herpesviridae which contains a linear, double-stranded DNA genome. The genome of the virus is encased by nucleocapsid protein which itself is surrounded by Tegument (a matrix layer) and lipid bilayer.[4,5] CMV infects people of all ages, and it is reported that by the age of 40, most people have had a CMV infection at some time of their life. Generally CMV infection does not show any symptoms but people with a weakend immune system, and infants with congenital infection are more prone to serious complications.[6,7] The symptoms of CMV infection widely vary from asymptomatic, to fever and fatigue, to severe symptoms that may result in damage to internal organs, the eyes and the brain. Though some anti-viral drugs are available, such as valganciclovir, ganciclovir, cidofovir, foscarnet, or a combination of these for the treatment of retinitis, those drugs may cause serious side effects and may not cure infection. A more general therapy, as well as a therapy with fewer or less serious side effects, is needed.[8-10]

Herpes Simplex Viruses (HSV-1 & HSV-2) belong to the family of Herpesviridae which contains linear, double-stranded DNA as genome. The genome of the Herpes Simplex Viruses are encased by icosahedrel shaped nucleocapsid protein which itself is surrounded by Tegument (a matrix layer) and lipid bilayer.[5,11] These viruses generally cause infections in the skin, eyes, lips and genitals. Symptoms include painful blisters or ulcers at the site of infection, a tingling sensation around mouth, genitalia and buttocks, swollen lymph nodes, fever and body aches. Herpes Simplex Viruses may also lead to meningitis and encephalitis in immune-compromised individuals and neonatal herpes in newborns.[11] According to recent WHO estimates, globally ~3.5 billion people have HSV-1[12,13] infection and ~0.5 billion people have HSV-2 infection.[14] Current antiviral medications for Herpes Simplex Viruses, such as acyclovir, famciclovir, and valacyclovir are used in the treatment of HSV infections, but are generally only effective in reducing the symptoms of the disease; they cannot cure the infections.[15,16]

Human Immunodeficiency Virus (HIV) belongs to the family of Retroviridae which contains two single-stranded RNA as its genome. The genome of the virus is encapsulated by nucleocapsid protein which itself is surrounded by a lipid-bilayer associated with Matrix protein.[17] HIV attacks the human immune system and causes Acquired Immuno Deficiency Syndrome (AIDS). Due to weakening of the immune system, people with AIDS are more prone to myriad infections that can be life threatening. Current therapies are available for the treatment of HIV infection, but none are able to cure the infection.[18,19]

Despite the high prevalence rate of viral infections, there are still very few approved drugs for the treatment and/or prophylaxis of envelope viral infections, such as those disclosed herein. In addition, current therapies still suffer from sub-optimal efficacy and severe toxicity, and are hampered by higher cost of treatment and the emergence of drug resistant strains.

Pharmaceutical companies are facing increasing challenges to expand their pipelines especially due to undruggable targets such as Protein-protein interactions.[20] Though Protein-protein interactions are part of the host-pathogen interaction, they also play a crucial role in many cellular functions of healthy cells. Modulating protein-protein interactions has been recognized as an attractive way of alleviating many diseases including inhibition of pathogen entry or replication.[21] However, it has been reported that small molecules are often inefficient at inhibit such interactions.[22] Though monoclonal antibodies are highly specific and potent in inhibiting or modulating these interactions, they often lack sufficient tissue or cellular penetration.[23] Without being bound by theory, it is believed herein that macrocyclic peptides with cell permeability could serve as a best solution. Macrocyclic peptides may also be the best option when considering that many viruses are highly mutative, and therefore, the drug that targets the protein—protein interactions should be flexible enough to withstand such mutation. Moreover, peptides offer many advantages over small molecules, including high specificity, selectivity, excellent potency and they are generally well tolerated.[24,25] Likewise, peptides may be favored over other macromolecules, such as antibodies, due to their lower manufacturing complexity and better target accessibility.[24] Without being bound by theory, it is believed herein that peptides may possess more advantages and overcome more limitations than either small molecules or large macromolecules.[24-30]

Novel peptide therapeutics (FPTs) with broad spectrum activity against influenza viruses have been discovered.[31,32] The mechanism of action of the FPTs against the influenza viruses was studied. Without being bound by theory, it is believed herein that the FPTs exert their action by binding and altering the integrity of the matrix proteins (M1) of the influenza viruses. It was subsequently discovered that the influenza virus matrix proteins share sufficient structural similarity with HIV, HSVs, RSV and CMV that FPTs are also active against those viruses and other enveloped viruses and matrix protein layer viruses.

SUMMARY OF THE INVENTION

It has been surprisingly discovered that peptides comprising the sequence twftfin are active against a wide variety of enveloped viruses and matrix protein layer viruses. It has also been surprisingly discovered that peptides comprising sequence variations of twftfin, where one or two other amino acids are independently inserted, deleted, or changed to a different D-amino acid, or to glycine, or to any L-amino acid are also highly active against a wide variety of enveloped viruses and matrix protein layer viruses. Peptides described herein generally exhibit antiviral activity that is many-fold better than peptides comprising an all L-amino acid sequence, and demonstrate broad spectrum activity against a wide variety of enveloped viruses and matrix protein layer viruses.

In one illustrative embodiment of invention, peptides, also referred to herein as FTPs, that include dextro or a mixture of dextro/levo-amino acids are described herein. In another embodiment, peptides that possess anti-viral properties against enveloped viruses or matrix protein layer viruses are described herein. In another embodiment, peptides that possess anti-viral properties against multiple enveloped viruses and matrix protein layer viruses are described herein. In another illustrative embodiment, uses of one or more of any of the peptides described herein for the manufacture of medicaments for treating or preventing enveloped virus and matrix protein layer virus infections are described. In another illustrative embodiment, pharmaceutical compositions, dosage forms, and dosage units, comprising one or more of any of the peptides described herein are described for use in treating or preventing enveloped virus and matrix protein layer virus infections. In another illustrative embodiment, methods for treating or preventing enveloped virus and matrix protein layer virus infections are described herein, where those methods include administering one or more of any of the peptides described herein, or pharmaceutical compositions, dosage forms, dosage units, and medicaments comprising those peptides.

In another embodiment, the enveloped virus or matrix protein layer virus is a retrovirus, lentivirus, paramyxovirus, flavivirus, hepatitis C virus, tick borne encephalitis, yellow fever, dengue fever virus, filovirus, togavirus, bunyavirus, herpesvirus, hepnavirus, paramyxovirus, or coronavirus. In another embodiment, the enveloped virus or matrix protein layer virus is herpes simplex virus, cytomegalovirus, respiratory syncytial virus, or human immunodeficiency virus. In another embodiment, the virus is HIV, Ebola, Marburg virus, rubella virus, hantavirus, arenavirus, cytomegalovirus, hepatitis B virus, or torovirus.

In another embodiment, the infection is AIDS, herpes, or SARS.

In another embodiment, peptides comprising the sequence tksrfX/xn (Formula I) are described herein. In another embodiment, peptides comprising the sequence tX/xsrfin (Formula II) are described herein. In another embodiment, peptides comprising the sequence twX/xrfin (Formula V) are described herein. In another embodiment, peptides comprising the sequence twfX/xfin (Formula VI) are described herein. In another embodiment, peptides comprising the sequence X/xwftfin (Formula VII) are described herein. In another embodiment, peptides comprising the sequence wwftfiX/x (Formula VIII) are described herein. In another embodiment, peptides comprising the sequence wwftX/xia (Formula IX) are described herein. In another embodiment, peptides comprising the sequence X/xwftfiX/x (Formula X) are described herein. In each of the foregoing, X/x is glycine, or any D-amino acid, or any L-amino acid.

In another embodiment, any of the peptides described herein also include an N-terminal and/or C-terminal cysteine residue. When both the N-terminus and C-terminus include cysteine residue, the peptide can be cyclized. It is to be understood that in every instance, the cysteine residue is independently selected from D-cysteine and L-cysteine.

In another embodiment, any of the peptides described herein also include one or more solubility tags. Illustratively, the solubility tag is included at the N-terminus and/or at the C-terminus. It is to be understood that the peptides described herein that include an N-terminal and/or C-terminal cysteine residue, including cyclic derivatives thereof, may also include one or more solubility tags. It is also to be understood that in every instance, each solubility tag is independently selected.

Additional details regarding FPTs are disclosed in PCT International Application Serial No. PCT/IB2016/057146, the entirety of the disclosure of which is incorporated herein by reference.

In another embodiment, analogues and derivatives of the peptides described herein are described. It is to be understood that the analogues and derivatives described herein do not include the peptides disclosed in PCT international publication No. WO 2009/151313. In another embodiment, peptides are described herein that do not include any of the sequences disclosed in PCT international publication No. WO 2009/151313.

As used herein, the term isolated peptide generally refers to a peptide that is ex-vivo, and/or in bulk form. It is to be understood that isolated peptides can be in admixture with other compounds, and/or in a solution or a suspension.

The sequences of peptides described herein are generally set forth using the conventional single letter code for each amino acid. Codes in uppercase letters correspond to the levo form of an amino acid, and codes in lowercase letters correspond to the dextro form of an amino acid. For example, the single letter code "A" denotes L-alanine, whereas the single letter code "a" denotes D-alanine; "R" denotes L-arginine, whereas "r" denotes D-arginine; and so-forth.

In another embodiment, an isolated peptide comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one or two of A1, A2, A3, A4, A5, A6, or A7 is optionally replaced with another D-amino acid, glycine, or any L-amino acid is described herein. In one variation, peptides where one or two of A1, A2, A3, A4, A5, A6, or A7 is replaced with the corresponding L-amino acid are described herein.

In another embodiment, an isolated peptide comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one of A1, A2, A3, A4, A5, A6, or A7 is optionally replaced with another D-amino acid, glycine or any L-amino acid is described herein. In one variation, peptides where one of A1, A2, A3, A4, A5, A6, or A7 is replaced with the corresponding L-amino acid are described herein.

In another embodiment, isolated anti-viral peptides comprising a sequence selected from twftfin, X/xwftfin, tX/xftfin, twX/xtfin, twfX/xfin, twftX/xin, twftfX/xn, twftfiX/x, and X/xwftfiX/x are described herein.

In another embodiment, isolated anti-viral peptides comprising a sequence selected from twftfin, X/xwftfin, tX/xftfin, twX/xtfin, twfX/xfin, twftX/xin, twftfX/xn, twftfiX/x, and X/xwftfiX/x, where in each sequence one additional amino acid is inserted, deleted, or changed to a different D-amino acid, or to glycine, or to any L-amino acid one amino acid are described herein.

In another embodiment, isolated anti-viral peptides comprising a sequence selected from PSP IV A17, PSP V A19 and PSP VI A1 are described herein.

In another embodiment, a peptide comprising a sequence shown in any of Tables 1-8 are described herein. It is to be understood that functional variants of the peptides in these Tables that retain biological activity are also within the scope of the invention described herein.

DETAILED DESCRIPTION

Figure 1:
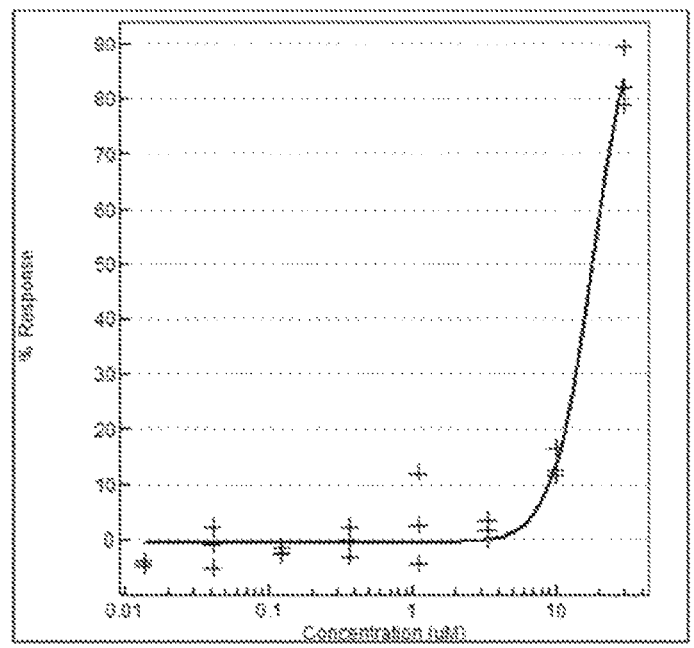
FIG. 1: Effect of H-RRKKcwwftfiac-OH (PSP VI A1) against RSV A2 in vitro. The ability of the peptide to inhibit the replication of RSV A2 was determined by CPE assay on Hep-2 cells. Experiments were done in triplicates and carried out in the presence of DMSO or increasing concentration of test compound.
Figure 2:
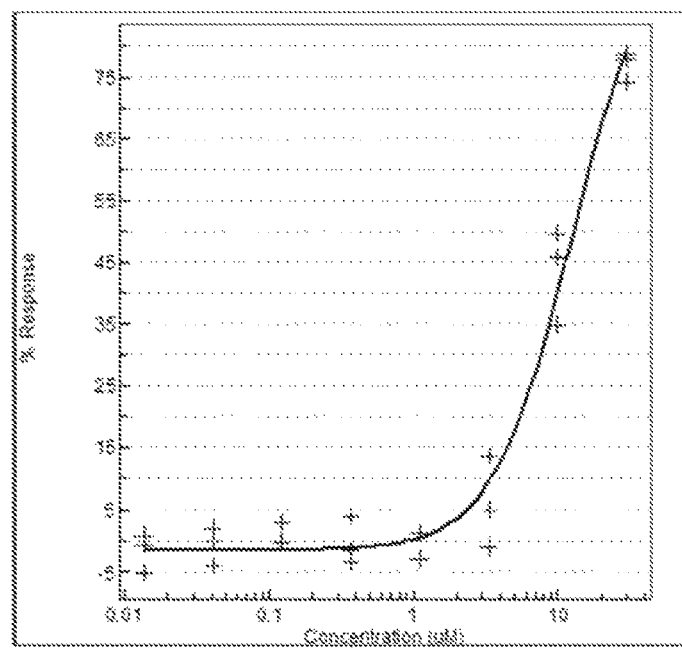
FIG. 2: Effect of H-RRKKctwftfinc-OH(PSP IV A17) against RSV A2 in vitro. The ability of the peptide to inhibit the replication of RSV A2 was determined by CPE assay on Hep-2 cells. Experiments were done in triplicates and carried out in the presence of DMSO or increasing concentration of test compound.
Figure 3:
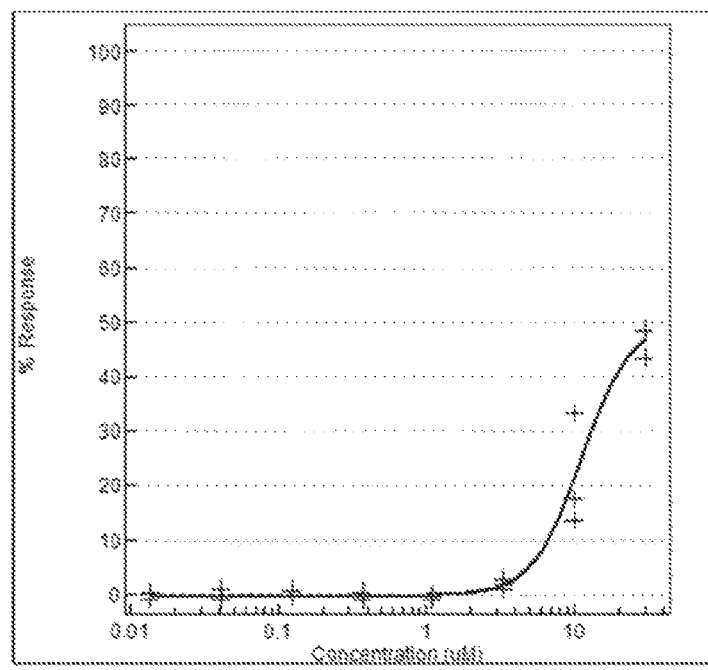
FIG. 3: Effect of PSP VI A1 against HSV-2 in vitro. The ability of the peptide to inhibit the replication of HSV was determined by CPE assay on Vero cells. Experiments were done in triplicates and carried out in the presence of DMSO or increasing concentration of test compound.
Figure 4:
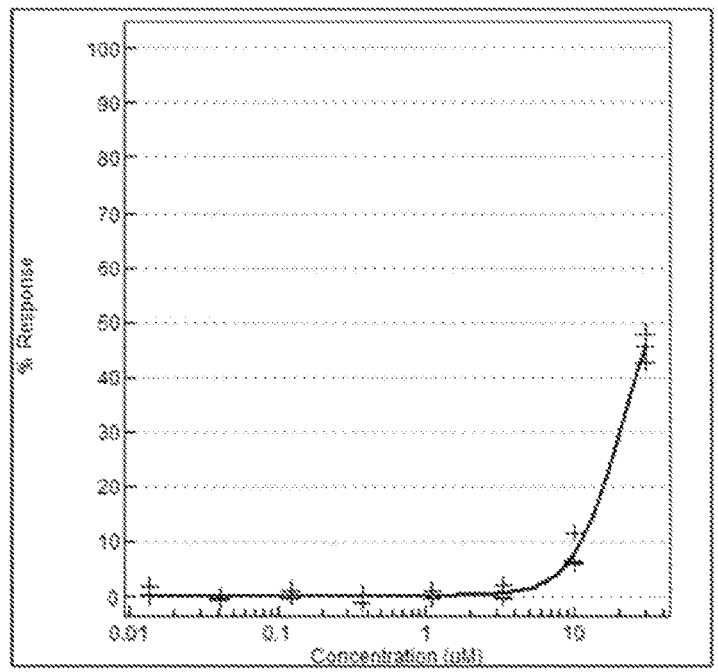
FIG. 4: Effect of PSP IV A17 against HSV-2 in vitro. The ability of the peptide to inhibit the replication of HSV was determined by CPE assay on Vero cells. Experiments were done in triplicates and carried out in the presence of DMSO or increasing concentration of test compound.
Figure 5:
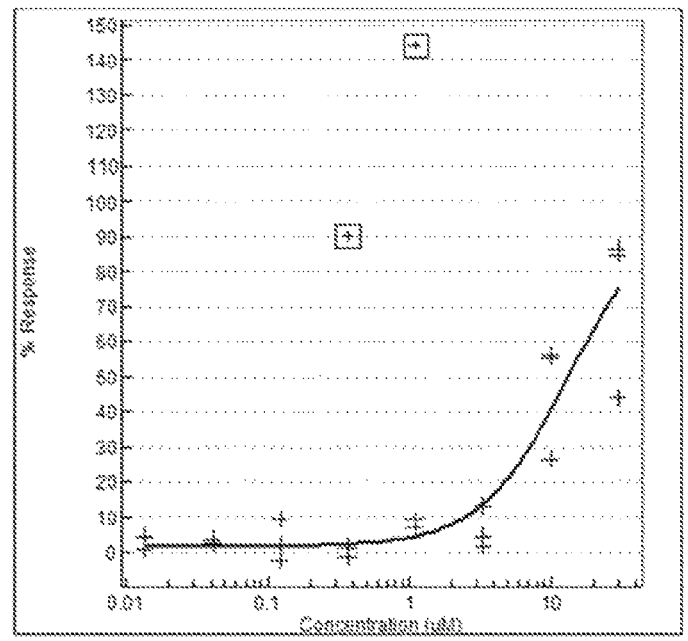
FIG. 5: Effect of PSP VI A1 against CMV in vitro. The ability of the peptide to inhibit the replication of CMV was determined by CPE assay on HFFF-2 cells. Experiments were done in triplicates and carried out in the presence of DMSO or increasing concentration of test compound.
Figure 6:
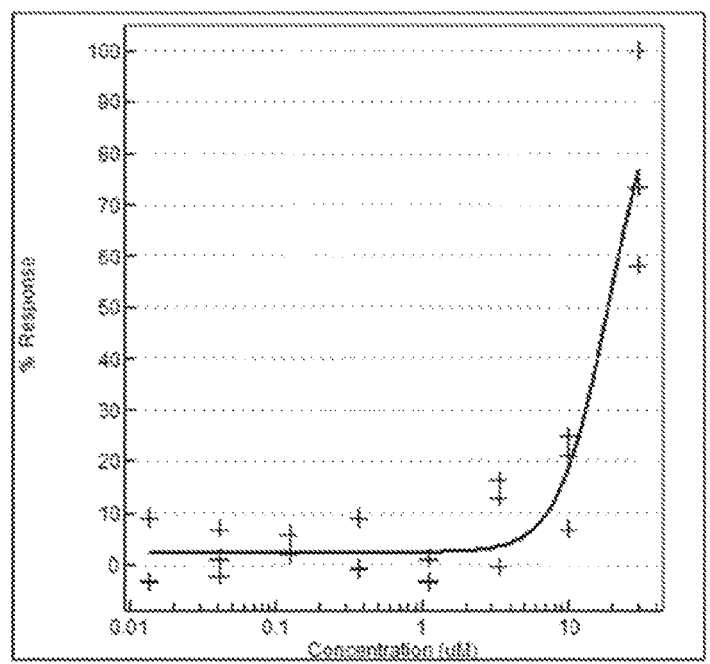
FIG. 6: Effect of PSP IV A17 against CMV in vitro. The ability of the peptide to inhibit the replication of CMV was determined by CPE assay on HFFF-2 cells. Experiments were done in triplicates and carried out in the presence of DMSO or increasing concentration of test compound.
Figure 7:
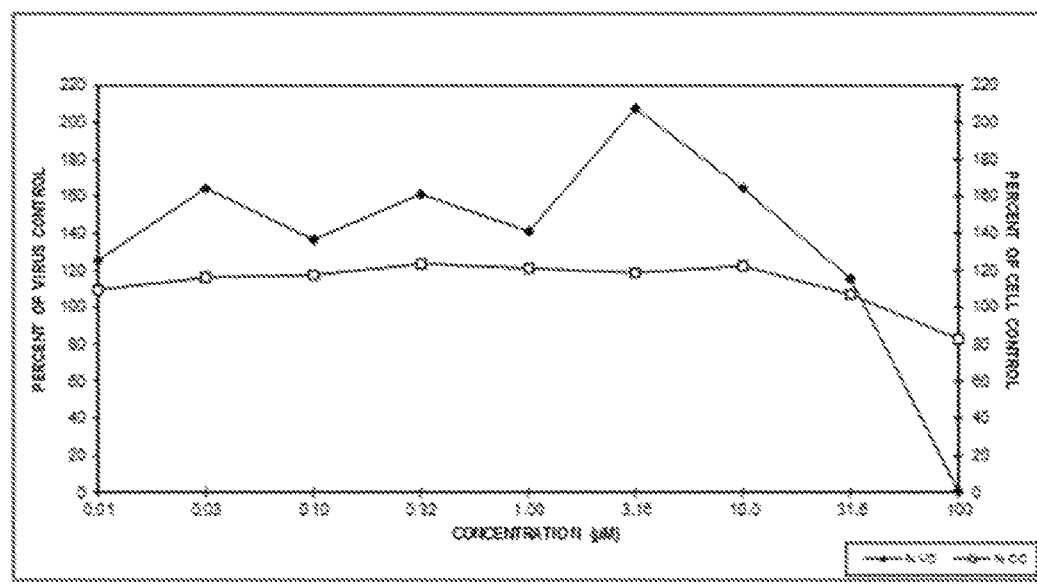
FIG. 7: Effect of PSP VI A1 against HIV-1 92UG029 in vitro. The ability of the peptide to inhibit the replication of HIV was determined by reverse transcriptase assay on PBMCs. Experiments were carried out in the presence of DMSO or increasing concentration of peptide. Results are presented as mean value of triplicate measurements.
Figure 8:
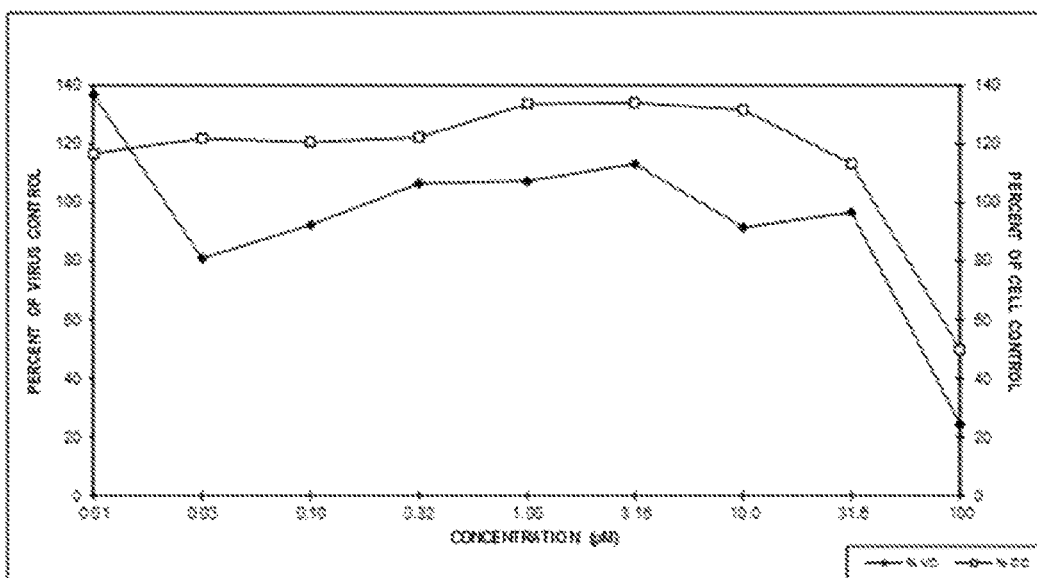
FIG. 8: Effect of H-cwwftfinc-OH (PSP V A19-C) against HIV-1 92UG029 in vitro. The ability of the peptide to inhibit the replication of HIV was determined by reverse transcriptase assay on PBMCs. Experiments were carried out in the presence of DMSO or increasing concentration of peptide. Results are presented as mean value of triplicate measurements.
Figure 9:
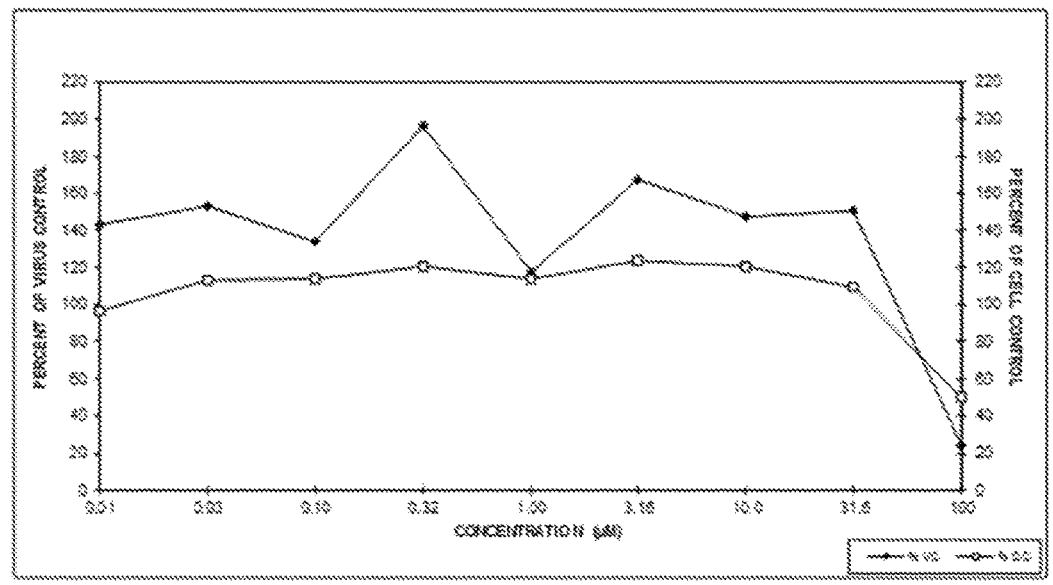
FIG. 9: Effect of H-RRKKtwftfin-OH (PSP IV A17-LS) against HIV-1 92UG029 in vitro. The ability of the peptide to inhibit the replication of HIV was determined by reverse transcriptase assay on PBMCs. Experiments were carried out in the presence of DMSO or increasing concentration of peptide. Results are presented as mean value of triplicate measurements.
Figure 10:
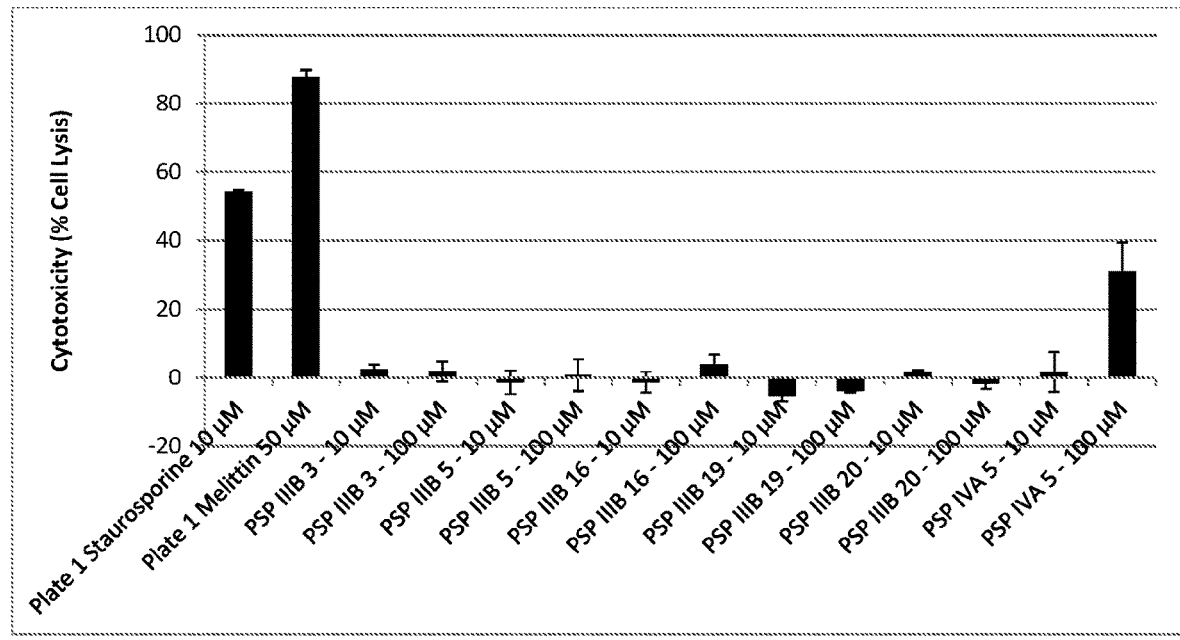
FIG. 10: Cytotoxic effects of anti-viral peptides in human hepatocytes. Cytotoxic effects of anti-viral peptides H-RRKKctwdrfinc-OH (PSP III B3), H-RRKKctwfrfinc-OH (PSP III B5), H-RRKKctwsrfinc-OH (PSP III B16), H-RRKKctwwrfinc-OH (PSP III B19), H-RRKKctwyrfinc-OH (PSP III B20), and H-RRKKctwfffinc-OH (PSP IV A5). Toxicity effects were tested in two different concentrations in human hepatic cell HepaRG™, a cell with a proven differentiated hepatocyte phenotype under the cell-culture conditions. Data are presented as the mean value±standard deviation of triplicate measurements. This experiment was performed as described in Example 3.
Figure 11:
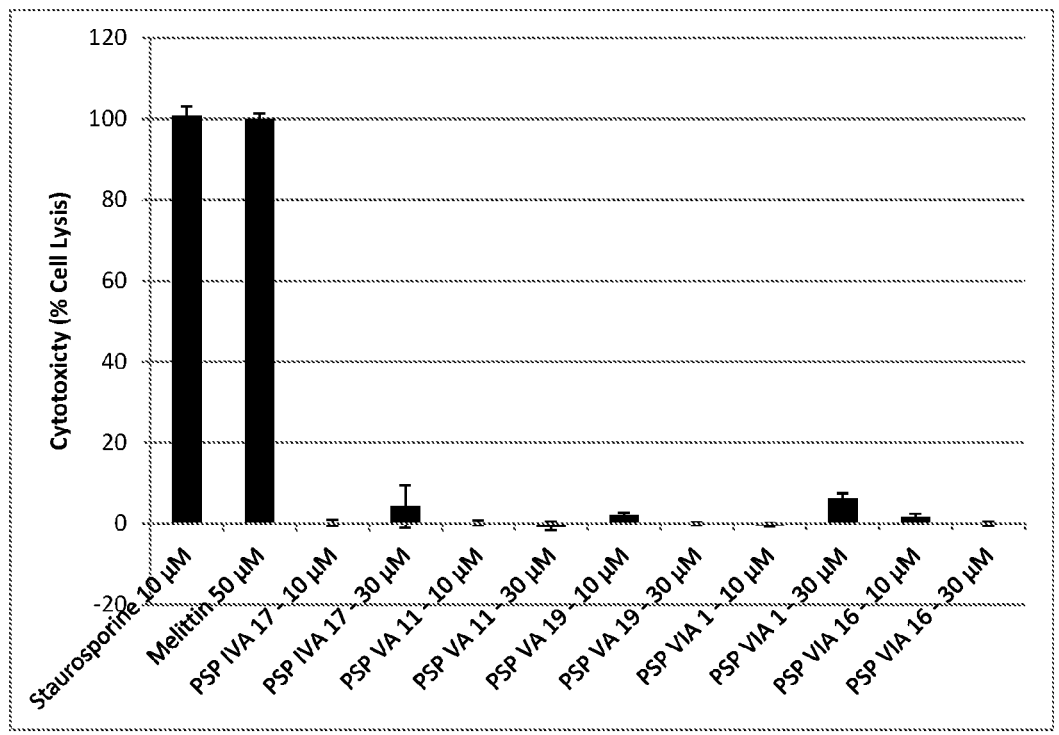
FIG. 11: Cytotoxic effects of anti-viral peptides in human hepatocytes. Cytotoxic effects of anti-viral peptides PSP IV A17, H-RRKKcwwftfinc-OH (PSP V A19), H-RRKKcmwftfinc-OH (PSP V A11), PSP VI A1, and H-RRKKcwwftfisc-OH (PSP VI A16). Toxicity effects were tested in two different concentrations in human hepatic cell HepaRG™, a cell with a proven differentiated hepatocyte phenotype under the cell-culture conditions. Data are presented as the mean value±standard deviation of triplicate measurements. This experiment was performed as described in Example 3.

The present invention will now be further described by the following illustrative embodiments. In the following passages, different illustrative aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. However, it is to be understood that the invention is not limited to such feature or features indicated as being preferred or advantageous, and any feature or features indicated as being preferred or advantageous are not required.

The practice of the present invention will employ, unless otherwise indicated, conventional techniques of chemistry, biochemistry, molecular biology, recombinant DNA technology, cell biology, immunology and bioinformatics which are within the skill of the art. Such techniques are explained fully in the literature.

Throughout this disclosure, a standard one letter code is used to denote the amino acids in accordance with IUPAC/IUB guidelines. In the sequences listed herein, the left most amino acid at the end of any sequence represents the amino-terminal end (optionally denoted with H—) whereas the right most amino acid represents the carboxy terminal end (optionally denoted with —OH). With the exception of glycine which is achiral, the levo form of amino acids is denoted in uppercase letters herein, and the dextro form of amino acids is denoted in lowercase letters. It is to be understood that unless indicated otherwise, references to L-amino acids include glycine.

The present invention is directed to peptides with anti-viral activity. In addition, the invention is directed to peptides with anti-viral activity against more than one envelope or matrix protein layer virus. In addition, the invention is directed to peptides with anti-viral activity against more than one envelope or matrix protein layer virus subtype. In addition, the invention is directed to pharmaceutical compositions comprising peptides described herein, and methods of using peptides described herein to prevent and/or treat viral infections.

Illustrative embodiments of the invention are described by the following clauses:

An isolated peptide of the sequence or comprising the sequence twftfin.

An isolated peptide of the sequence or comprising the sequence of an analog or derivative of twftfin.

An isolated peptide of the sequence or comprising the sequence A1-A2-A3-A4-A5-A6-A7, where A1 is t or w, A2 is k or w, A3 is s or f, A4 is r or t, A5 is f, h, n, or w, A6 is i or d, and A7 is n or a, and where any one or any two of A1, A2, A3, A4, A5, A6, or A7 is optionally replaced with another D-amino acid or L-amino acid.

An isolated peptide of the sequence or comprising the sequence A1-A2-A3-A4-A5-A6-A7, where A1 is t or w, A2 is k or w, A3 is s or f, A4 is r or t, A5 is h, i, n, or w, A6 is i or d, and A7 is n or a, and where any one or any two of A1, A2, A3, A4, A5, A6, or A7 is optionally replaced with another D-amino acid or L-amino acid.

The peptide of the preceding clause wherein one or two of A1, A2, A3, A4, A5, A6, or A7 is replaced with the corresponding L-amino acid.

An isolated peptide of the sequence or comprising the sequence A1-A2-A3-A4-A5-A6-A7, where A1 is t or w, A2 is k or w, A3 is s or f, A4 is r or t, A5 is i or w, A6 is i or d, and A7 is n or a, and where any one or any two of A1, A2, A3, A4, A5, A6, or A7 is optionally replaced with another D-amino acid or L-amino acid.

The peptide of the preceding clause wherein one or two of A1, A2, A3, A4, A5, A6, or A7 is replaced with the corresponding L-amino acid.

The peptide of any one of the preceding clauses where any one of A1, A2, A3, A4, A5, A6, or A7 is optionally replaced with another D-amino acid or L-amino acid.

The peptide of the preceding clause wherein one of A1, A2, A3, A4, A5, A6, or A7 is replaced with the corresponding L-amino acid.

The peptide of any of the preceding clauses wherein A1 is t.

The peptide of any of the preceding clauses wherein A1-A2 is tk or tw.

The peptide of any of the preceding clauses wherein A2-A3 is ks or wf.

The peptide of any of the preceding clauses wherein A1-A2-A3 is tks or twf.

The peptide of any of the preceding clauses wherein A3-A4 is sr or ft.

The peptide of any of the preceding clauses wherein A2-A3-A4 is ksr or wft.

The peptide of any of the preceding clauses wherein A4 is r or t.

The peptide of any of the preceding clauses wherein A5 is f, h, i, n, or w.

The peptide of any of the preceding clauses wherein A5 is h, i, n, or w.

The peptide of any of the preceding clauses wherein A5 is i or w.

The peptide of any of the preceding clauses wherein A5 is f.

The peptide of any of the preceding clauses wherein A1-A2 is ww.

The peptide of any of the preceding clauses wherein A6-A7 is ia.

The peptide of any of the preceding clauses wherein A4 is r or t, and A6 is i.

The peptide of any of the preceding clauses wherein A6-A7 is in.

The peptide of any of the preceding clauses wherein A7 is n.

The peptide of any of the preceding clauses comprising tksrfX/xn, where X/x is i, l, or y.

The peptide of any of the preceding clauses comprising twfX/xfin, where X/x is i, l, m, r, s, t, v, or w.

The peptide of any of the preceding clauses comprising twX/xrfin, where X/x is a, c, e, f, G, h, k, l, m, n, p, q, r, s, t, v, w, or y.

The peptide of any of the preceding clauses comprising tX/xsrfin, where X/x is p, r, s, or w.

The peptide of any of the preceding clauses comprising X/xwftfin, where X/x is m or w.

The peptide of any of the preceding clauses comprising wwftX/xia, where X/x is h, n, or w.

The peptide of any of the preceding clauses comprising wwftX/xia, where X/x is i or w.

The peptide of any of the preceding clauses comprising a sequence selected from tksrfX/xn, tX/xsrfin, twX/xrfin, twfX/xfin, X/xwftfin, wwftfiX/x, wwftX/xia, and tksrfdn or a derivative thereof, where X/x is glycine, or any D-amino acid, or any L-amino acid.

The peptide of any of the preceding clauses comprising a sequence selected from twftfin, X/xwftfin, tX/xftfin, twX/xtfin, twfX/xfin, twftX/xin, twftfX/xn, twftfiX/x, and X/xwftfiX/x, where X/x is glycine, or any D-amino acid, or any L-amino acid.

The peptide of any of the preceding clauses comprising a sequence selected from twftfin, X/xwftfin, tX/xftfin, twX/xtfin, twfX/xfin, twftX/xin, twftfX/xn, twftfiX/x, and X/xwftfiX/x, where X/x is glycine, or any D-amino acid, or any L-amino acid, and where in each sequence one additional amino acid is inserted, deleted, or changed to a different D-amino acid, or to glycine, or to any L-amino acid one amino acid.

The peptide of any of the preceding clauses comprising a sequence selected from PSP IV A17, PSP V A19 and PSP VI A1.

The peptide of any of the preceding clauses comprising the sequence tksrfX/xn (Formula I).

The peptide of any of the preceding clauses comprising the sequence tX/xsrfin (Formula II).

The peptide of any of the preceding clauses comprising the sequence twX/xrfin (Formula V).

The peptide of any of the preceding clauses comprising the sequence twfX/xfin (Formula VI).

The peptide of any of the preceding clauses comprising the sequence X/xwftfin (Formula VII).

The peptide of any of the preceding clauses comprising the sequence wwftfiX/x (Formula VIII).

The peptide of any of the preceding clauses comprising the sequence wwftX/xia (Formula IX).

The peptide of any of the preceding clauses comprising the sequence X/xwftfiX/x (Formula X).

The peptide of any of the preceding clauses further comprising an N-terminal and/or C-terminal cysteine residue.

The peptide of the preceding clause in cyclic form.

The peptide of any of the preceding clauses further comprising one or more solubility tags, each of which is independently selected.

The peptide of the preceding clause wherein the solubility tag is at the N-terminus and/or at the C-terminus.

The peptide of any one of the preceding clauses wherein the solubility tag is selected from RRKK and rrkk.

The peptide of any one of the preceding or following clauses wherein the peptide has anti-viral activity against a retrovirus, lentivirus, paramyxovirus, flavivirus, hepatitis C virus, tick borne encephalitis, yellow fever, dengue fever virus, filovirus, togavirus, bunyavirus, herpesvirus, hepnavirus, paramyxovirus, or coronavirus.

The peptide of any one of the preceding or following clauses wherein the peptide has anti-viral activity against herpes simplex virus, cytomegalovirus, respiratory syncytial virus, or human immunodeficiency virus.

The peptide of any one of the preceding or following clauses wherein the peptide has anti-viral activity against HIV, Ebola, Marburg virus, rubella virus, hantavirus, arenavirus, cytomegalovirus, hepatitis B virus, or torovirus.

The peptide of any one of the preceding or following clauses wherein the infection is AIDS, herpes, or SARS.

The peptide of any one of the preceding or following clauses wherein the peptide has anti-viral activity against herpes simplex virus, cytomegalovirus, respiratory syncytial virus, and/or human immunodeficiency virus.

The peptide of any one of the preceding or following clauses which has an $IC_{50}$ of less than 100 μM against the virus.

The peptide of any one of the preceding clauses wherein X/x is selected from any proteinogenic amino acid.

The peptide of any one of the preceding clauses wherein X/x is selected from the D-isomer of any proteinogenic amino acid.

The peptide of any one of the preceding clauses selected from ctksrfX/xnc, rrkkctX/xsrfinc, RRKKctwX/xrfinc, RRKKawfX/xfinc, RRKKcX/xwftfinc, RRKKcwwftfiX/xc, RRKKcwwftX/xiac, and ctksrfdnc.

The peptide of any one of the preceding clauses wherein x is selected from a, c, d, e, f, h, i, k, l, m, n, p, q, r, s, t, v, w, y or G.

The peptide of any one of the preceding clauses wherein the peptide comprises the sequence RRKKctwX/xrfinc, or is selected from RRKKctwarfinc, RRKKctwcrfinc, RRKKctwdrfinc, RRKKctwerfinc, RRKKctwfrfinc, RRKKctwGrfinc, RRKKctwhrfinc, RRKKctwirfinc, RRKKctwkrfinc, RRKKctwlrfinc, RRKKctwmrfinc, RRKKctwnrfinc, RRKKctwprfinc, RRKKctwqrfinc, RRKKctwrrfinc, RRKKctwsrfinc, RRKKctwtrfinc, RRKKctwvrfinc, RRKKctwwrfinc or RRKKctwyrfinc.

The peptide of any one of the preceding clauses wherein the peptide comprises the sequence RRKKawfX/xfinc, or is selected from RRKKctwfafinc, RRKKctwfcfinc, RRKKctwfdfinc, RRKKctwfefinc, RRKKctwfffinc, RRKKctwfGfinc, RRKKctwfhfinc, RRKKctwfifinc, RRKKctwfkfinc, RRKKctwflfinc, RRKKctwfmfinc, RRKKctwfnfinc, RRKKctwfpfinc, RRKKctwfqfinc, RRKKctwfrfinc, RRKKctwfsfinc, RRKKctwftfinc, RRKKctwfvfinc, RRKKctwfwfinc, and RRKKctwfyfinc.

The peptide of any one of the preceding clauses wherein the peptide comprises the sequence RRKKcX/xwftfinc, or is selected from RRKKcawftfinc, RRKKccwftfinc, RRKKcdwftfinc, RRKKcewftfinc, RRKKcfwftfinc, RRKKcGwftfinc, RRKKchwftfinc, RRKKciwftfinc, RRKKckwftfinc, RRKKclwftfinc, RRKKcmwftfinc, RRKKcnwftfinc, RRKKcpwftfinc, RRKKcqwftfinc, RRKKcrwftfinc, RRKKcswftfinc, RRKKctwftfinc, RRKKcvwftfinc, RRKKcwwftfinc and RRKKcywftfinc.

The peptide of any one of the preceding clauses wherein the peptide comprises the sequence RRKKcwwftfiX/xc, or is selected from RRKKcwwftfiac, RRKKcwwftficc, RRKKcwwftfidc, RRKKcwwftfiec, RRKKcwwftfifc, RRKKcwwftfiGc, RRKKcwwftfihc, RRKKcwwftfiic, RRKKcwwftfikc, RRKKcwwftfilc, RRKKcwwftfimc, RRKKcwwftfipc, RRKKcwwftfiqc, RRKKcwwftfirc, RRKKcwwftfisc, RRKKcwwftfitc, RRKKcwwftfivc, RRKKcwwftfiwc, RRKKcwwftfiyc.

The peptide of any one of the preceding clauses wherein the peptide is selected from ctksrfanc, ctksrfcnc, ctksrfdnc, ctksrfenc, ctksrffnc, ctksrfGnc, ctksrfhnc, ctksrfinc, ctksrfknc, ctksrflnc, ctksrfmnc, ctksrfnnc, ctksrfpnc, ctksrfqnc, ctksrfrnc, ctksrfsnc, ctksrftnc, ctksrfvnc, ctksrfwnc and ctksrfync.

The peptide of any one of the preceding clauses wherein the peptide is selected from rrkkctasrfinc, rrkkctcsrfinc, rrkkctdsrfinc, rrkkctesrfinc, rrkkctfsrfinc, rrkkctGsrfinc, rrkkcthsrfinc, rrkkctisrfinc, rrkkctksrfinc, rrkkctlsrfinc, rrkkctmsrfinc, rrkkctnsrfinc, rrkkctpsrfinc, rrkkctqsrfinc, rrkkctrsrfinc, rrkkctssrfinc, rrkkcttsrfinc, rrkkctvsrfinc, rrkkctwsrfinc and rrkkctysrfinc.

The peptide of any one of the preceding clauses wherein the peptide is selected from RRKKcwwftaiac, RRKKcwwftciac, RRKKcwwftdiac, RRKKcwwfteiac, RRKKcwwftGiac, RRKKcwwfthiac, RRKKcwwftiiac, RRKKcwwftkiac, RRKKcwwftliac, RRKKcwwftmiac, RRKKcwwftniac, RRKKcwwftpiac, RRKKcwwftqiac, RRKKcwwftriac, RRKKcwwftsiac, RRKKcwwftviac, RRKKcwwftwiac, and RRKKcwwftyiac.

The peptide of any one of the preceding clauses wherein the peptide comprises twfrfin, twfffin, twftfin, wwftfin, and wwftfia.

The peptide of any one of the preceding clauses wherein the peptide comprises ctwfrfinc, ctwfffinc, ctwftfinc, cwwftfinc and cwwftfiac.

The peptide of any one of the preceding clauses wherein the peptide is selected from RRKKctwfrfinc, RRKKctwff-finc, RRKKctwftfinc, RRKKcwwftfinc and RRKKcwwft-fiac.

The peptide of any one of the preceding clauses for use in the manufacture of a medicament.

The peptide of any one of the preceding clauses for use as a medicament.

A pharmaceutical composition comprising the peptide of any one of the preceding clauses.

The peptide of any one of the preceding clauses or a pharmaceutical composition thereof adapted for use in the treatment of virus infection.

Use of the peptide of any one of the preceding clauses or a pharmaceutical composition thereof in the manufacture of a medicament for the treatment of virus infection.

A method for treating virus infection in a host animal, the method comprising administering a therapeutically effective amount of the peptide of any one of the preceding clauses or a pharmaceutical composition thereof to the host animal.

The method of any one of the preceding clauses wherein the peptide or pharmaceutical composition is administered by a nasal, pulmonary, intrabronchial, oral or parenteral route.

The method of any one of the preceding clauses wherein the peptide or pharmaceutical composition is administered prophylactically.

A method for detecting a peptide that has antiviral activity comprising making a derivative of the peptide of any one of the preceding clauses and screening for antiviral activity.

A kit comprising the peptide of any one of the preceding clauses or a pharmaceutical composition thereof and instructions for use of the peptide or pharmaceutical composition for treating a virus infection.

A vector comprising a nucleic acid encoding the peptide of any one of the preceding clauses.

A plasmid comprising a nucleic acid encoding the peptide of any one of the preceding clauses.

A host cell expressing the peptide of any one of the preceding clauses.

A combination comprising the peptide of any one of the preceding clauses and a second agent selected from a nucleic acid, peptide, protein, contrast agent, antibody, toxin and small molecule.

A recombinant library comprising the peptide of any one of the preceding clauses.

Without being bound by theory, it is also believed herein that peptides disclosed herein contain membrane transiting motifs which disrupt the lipid envelopes of the viruses in order to gain access to the underlying matrix proteins which may play a crucial role in their anti-viral activity. Hence the peptides of the present invention are expected to bind and inhibit any lipid envelope containing viruses including, but not limited to, the Togaviridae including rubella virus; the Retroviridae, including lentiviruses, such as HIV; Bunyaviridae such as hantaviruses and arenaviruses; Herpesviridae such as herpes viruses and cytomegaloviruses; Hepnaviridae such as hepatitis B viruses; Paramyxoviridae such as paramyxoviruses; Flaviviridae such as flavivirus, hepatitis C virus, tick borne encephalitis, yellow fever and dengue fever viruses; Filoviridae such as Ebola and Marburg viruses; and Coronaviridae such as coronaviruses including SARS virus and toroviruses.

Derivatives of twftfin include peptides wherein one or more amino acids are deleted or substituted with a different amino acid as shown in Table 1. Derivatives also include peptides with at least 80%, 85%, 90% or 95% sequence identity. Derivatives preferably comprise, consist essentially of, or consist of 7 amino acids. In another embodiment, the derivative comprises a core peptide of 7 amino acids and further comprises additional amino acids to improve various properties, solubility or enable cyclization as described herein. The core peptide is the active peptide, that is the peptide that confers antiviral activity. Derivatives are functional, that is they are biologically active and demonstrate antiviral properties, preferably against more than one virus.

The term "peptide" as used herein refers to a polymer that includes amino acid residues. In illustrative embodiments, the peptide includes from 2 to about 100 residues or 2 to about 50 residues. In other embodiments, the peptide includes about 7 to 20 residues, for example 7 to 10, 11, 12, 13, 14, 15, 16, 17, 18 or 19 residues. In certain embodiments, the amino acid residues comprising the peptide are all "D-form" amino acid residues, however, it is recognized that in various embodiments, "L" amino acids can be incorporated into the peptide. Thus, in some embodiments, the peptides of the invention are a mixture of D-form and L-form amino acids. For example, the peptide may comprise a core of 7 D-amino acids wherein one or more amino acids may be in the L form.

Peptides also include amino acid polymers in which one or more amino acid residues is an artificial chemical analogue of a corresponding naturally occurring amino acid, or the D-amino acid analogue, as well as naturally occurring amino acid polymers. In addition, the term applies to amino acids joined by a peptide linkage or by other, "modified linkages" (e.g. where the peptide bond is replaced by an α-ester, a β-ester, a thioamide, phosphonamide, carbamate, hydroxylate, and the like).

In certain embodiments, peptides of the invention comprise an active core peptide with 7 residues. Additionally, the peptide may comprise further residues, including but not limited to one or more residues that may allow the peptide to form a cyclic peptide and/or one or more residues that increase solubility of the peptide as described herein.

Peptides described herein can be naturally occurring or not naturally occurring. They can be a) produced by chemical synthesis, b) produced by recombinant DNA technology, c) produced by biochemical or enzymatic fragmentation of larger molecules, d) produced by combination of any of the methods listed above from a to d, e) produced by any other means for producing peptides. In another embodiment, the peptide is not naturally occurring. In another embodiment, the peptide comprises a modification that is not naturally occurring. Examples of such modifications are described herein.

TABLE 1

Illustrative families of twftfin derivatives; the
N and C terminus is shown for clarification.

| Series No. | Group | Core Sequence | Illustrative Peptide Sequence |
|---|---|---|---|
| 1 | PSP IV A | twftfin | H-ctwftfinc-OH6) |
| 2 | P1-RI-CD | tksrfdn | H-ctksrfdnc-OH) |
| 3 | PSP | tksrfX/xn Formula I | H-ctksrfX/xnc-OH |
| 4 | PSP II A | tX/xsrfin Formula II | H-rrkkctX/xsrfinc-OH |
| 5 | PSP III B | twX/xrfin Formula V | H-RRKKctwX/xrfinc-OH |
| 6 | PSP IV A | twfX/xfin Formula VI | H-RRKKctwfX/xfinc-OH |
| 7 | PSP V A | X/xwftfin Formula VII | H-RRKKcX/xwftfinc-OH |
| 8 | PSP VI A | wwftfiX/x Formula VIII | H-RRKKcwwftfiX/xc-OH |
| 9 | PSP VII A | wwftX/xia Formula IX | H-RRKKcwwftX/xiac-OH |
| 10 | PSP X A | X/xwftfiX/x Formula X | H-RRKKcX/xwftfiX/xc-OH |

In another embodiment, an anti-viral peptide comprising, consisting essentially of, or consisting of a sequence selected from tksrfX/xn, tX/xsrfin, twX/xrfin, twfX/xfin, X/xwftfin, wwftfiX/x, wwftX/xia, and tksrfdn is described. In another embodiment, an anti-viral peptide comprising, consisting essentially of, or consisting of a sequence selected from tksrfX/xn, tX/xsrfin, twX/xrfin, twfX/xfin, X/xwftfin, wwftfiX/x, and wwftX/xia is described.

In another embodiment, an anti-viral peptide comprising, consisting essentially of, or consisting of a sequence selected from twftfin, X/xwftfin, tX/xftfin, twX/xtfin, twfX/xfin, twftX/xin, twftfX/xn, twftfiX/x, and X/xwftfiX/x, where X/x is glycine, or any D-amino acid, or any L-amino acid is described.

In another embodiment, an anti-viral peptide comprising, consisting essentially of, or consisting of a sequence selected from twftfin, X/xwftfin, tX/xftfin, twX/xtfin, twfX/xfin, twftX/xin, twftfX/xn, twftfiX/x, and X/xwftfiX/x, where X/x is glycine, or any D-amino acid, or any L-amino acid, and where in each sequence one additional amino acid is inserted, deleted, or changed to a different D-amino acid, or to glycine, or to any L-amino acid one amino acid is described.

In another embodiment, an anti-viral peptide comprising, consisting essentially of, or consisting of a sequence selected from ctksrfX/xnc, ctX/xsrfinc, ctwX/xrfinc, ctwfX/xfinc, cX/xwftfinc, cwwftfiX/xc, cwwftX/xiac, and ctksrfdnc is described. In another embodiment, an anti-viral peptide comprising, consisting essentially of, or consisting of a sequence selected from ctksrfX/xnc, ctX/xsrfinc, ctwX/xrfinc, ctwfX/xfinc, cX/xwftfinc, cwwftfiX/xc, and cwwftX/xiac is described.

In another embodiment, an anti-viral peptide comprising, consisting essentially of, or consisting of a sequence selected from RRKKctksrfX/xnc, RRKKaX/xsrfinc, RRKKetwX/xrfinc, RRKKawfX/xfinc, RRKKcX/xwftfinc, RRKKcwwftfiX/xc, RRKKcwwftX/xiac, and RRKKctksrfdnc is described. In another embodiment, an anti-viral peptide comprising, consisting essentially of, or consisting of a sequence selected from RRKKaksrfX/xnc, RRKKctX/xsrfinc, RRKKctwX/xrfinc, RRKKawfX/xfinc, RRKKcX/xwftfinc, RRKKcwwftfiX/xc, and RRKKcwwftX/xiac is described.

In another embodiment, an anti-viral peptide comprising, consisting essentially of, or consisting of a sequence selected from rrkkaksrfX/xnc, rrkkctX/xsrfinc, rrkketwX/xrfinc, rrkkawfX/xfinc, rrkkcX/xwftfinc, rrkkcwwftfiX/xc, rrkkcwwftX/xiac, and rrkkctksrfdnc is described. In another embodiment, an anti-viral peptide comprising, consisting essentially of, or consisting of a sequence selected from rrkkaksrfX/xnc, rrkkctX/xsrfinc, rrkketwX/xrfinc, rrkkawfX/xfinc, rrkkcX/xwftfinc, rrkkcwwftfiX/xc, and rrkkcwwftX/xiac is described.

It is to be understood that in any of the foregoing embodiments, the D-cysteine can be L-cysteine.

In the sequences described herein, the amino acid designation "X/x" represents the position where a substitution is made, which may include any L-amino acid or D-amino acid, or any amino acid analogue. The letter "X/x" denotes any proteinogenic amino acid, that is any one of 20 naturally occurring amino acids. With the exception of G which is achiral, X denotes an amino acid in the L form and x denotes an amino acid in the D form. In another embodiment, X/x is x, that is an amino acid in the D form, or X, that is an amino acid in the L form. In another embodiment, x is selected from the following amino acids in the D form: a, c, d, e, f, h, i, k, l, m, n, p, q, r, s, t, v, w, or y. In another embodiment, X is selected from the following amino acids in the L form: A, C, D, E, F, H, I, K, L, M, N, P, Q, R, S, T, V, W or Y. In another embodiment, X is glycine.

In another embodiment, the peptide has an $IC_{50}$ of less than 100 µM or less than 50 µM, or less than 10 µM, or less than 5 µM, or less than 1 µM, or less than 0.1 µM. In another embodiment, the peptide shows at least 10%, 20%, 30%, 40%, 50%, 60%, 70%, 80%, 90%, 95% or more inhibition of at least one virus and/or at least one virus subtype, preferably of at least two viruses and/or at least two virus subtypes. Preferably, inhibition is at least 50%, 60%, 70%, 80%, 90%, 95% or more, or at least 75%, 80%, 90%, 95% or more.

In another embodiment, the peptide has antiviral activity against preferably 2, 3, 4 or more viruses and/or virus subtypes as measured using, for example, 0.01 µM to 100 µM of a peptide in a plaque reduction assay on MDCK cells. In another embodiment, the peptide shows at least 75%, 80%, 90% or 95% inhibition of at least two virus subtypes.

In another embodiment, the peptide of the invention comprises one or more solubility tags. In one illustrative embodiment, a solubility tag is a short peptide made up of charged amino acids, that, when covalently attached to N-terminal or C-terminal end of a hydrophobic peptide, will increase the solubility of the linked peptide. For example, the solubility tag may comprise one or more amino acid selected from D, E, H, K, N, Q, R, S, T, hydroxy-proline and pyro-glutamic acid as these possess hydrophilic characters. These can be either in levo or dextro form. Adding any of these amino-acids in any combination or repetition, either at N terminal or C terminal end, especially E/D/R/K, can be used to increase the solubility of a peptide. Solubility can also be increased by adding the dipeptide EE, the tripeptide SGS and/or with Hyperglycosylation and PEGylation or other methods known in the art for increasing solubility.

For example, the solubility tag may comprise or consist of solubility tag RRKK (either in levo form RRKK or dextro form rrkk) attached to the N and/or C terminal end of the peptide.

The peptide of the invention may be in linear or in cyclic form. In another embodiment, the peptide of the invention is in cyclic form. The peptides can be cyclized, for example, by formation of a disulfide bond between cysteine residues (or, more generally, between two of the at least two cysteine residues present in the polypeptide (e.g., at the terminal regions)). It is to be understood that each cysteine residue is independently D-cysteine or L-cysteine. For example, one can add at least two cysteine residues, one or both of which are, optionally, at the C-terminal or N-terminal of the peptide. Thus, the anti-viral peptides as well as their derivatives may be cyclized by disulfide bond with their terminal cysteine residues. As shown herein, linear versions of the peptides (i.e. without any cyclization) show anti-viral properties. It is also to be understood that where a peptide contains three or more cysteine residues, one or more of the residues may be modified in order to prevent that residue from participating in formation of a disulfide bond. Conveniently this may be achieved by protecting the thiol group of the cysteine with acetamidomethyl, to form the cysteine analogue acetamidomethyl-cysteine (Cys(Acm)). In the context of the peptides of the present invention, this may be done with the internal cysteine residues. Modification can be carried out during synthesis (i.e., the modified residue is used for synthesis), or may be carried out post-synthesis.

Strategies for the preparation of cyclic polypeptides from linear precursors have been described and can be employed with the present peptides. For example, approaches include chemical cross-linking, chemical intramolecular ligation methods and enzymatic intramolecular ligation methods, which allow linear synthetic peptides to be efficiently cyclized under aqueous conditions.

In another embodiment, peptides in cyclic form and comprising a solubility tag, for example RRKK (either in levo or dextro form) are described herein.

In another embodiment, the peptide is selected from ctksrfX/xnc, rrkkaX/xsrfinc, RRKKetwX/xrfinc, RRKKawfX/xfinc, RRKKcX/wftfinc or RRKKcwwftfiX/xc, RRKKcwwwftX/xiac, or ctksrfdnc.

In another embodiment, the peptide of the invention comprises the general sequence twX/xrfin (Formula V), where X/x is a, c, d, e, f, l, m, n, p, q, r, s, t, v, w, or y. The peptide may comprise a cysteine residue at the N and C terminal end for cyclisation and/or a solubility tag. In another embodiment, the peptide is selected from RRKKctwarfinc, RRKKctwcrfinc, RRKKctwdrfinc, RRKKctwerfinc, RRKKctwfrfinc, RRKKctwGrfinc, RRKKctwhrfinc, RRKKctwirfinc, RRKKctwkrfinc, RRKKctwlrfinc, RRKKctwmrfinc, RRKKctwnrfinc, RRKKctwprfinc, RRKKctwqrfinc, RRKKctwrrfinc, RRKKctwsrfinc, RRKKctwtrfinc, RRKKctwvrfinc, RRKKctwwrfinc or RRKKctwyrfinc. Also within the scope of the invention are peptides as shown above wherein the solubility tag is in the D form (rrkk). Also within the scope of the invention are functional derivatives of these peptides which are without any cyclization.

TABLE 2

Illustrative peptides.

| FPT ID | Sequence |
| --- | --- |
| PSP III B1 | H-RRKKctwarfinc-OH |
| PSP III B2 | H-RRKKctwcrfinc-OH |
| PSP III B3 | H-RRKKctwdrfinc-OH |
| PSP III B4 | H-RRKKctwerfinc-OH |
| PSP III B5 | H-RRKKctwfrfinc-OH |
| PSP III B6 | H-RRKKctwGrfinc-OH |
| PSP III B7 | H-RRKKctwhrfinc-OH |
| PSP III B8 | H-RRKKctwirfinc-OH |
| PSP III B9 | H-RRKKctwkrfinc-OH |
| PSP III B10 | H-RRKKctwlrfinc-OH |
| PSP III B11 | H-RRKKctwmrfinc-OH |
| PSP III B12 | H-RRKKctwnrfinc-OH |
| PSP III B13 | H-RRKKctwprfinc-OH |
| PSP III B14 | H-RRKKctwqrfinc-OH |
| PSP III B15 | H-RRKKctwrrfinc-OH |
| PSP III B16 | H-RRKKctwsrfinc-OH |
| PSP III B17 | H-RRKKctwtrfinc-OH |
| PSP III B18 | H-RRKKctwvrfinc-OH |
| PSP III B19 | H-RRKKctwwrfinc-OH |
| PSP III B20 | H-RRKKctwyrfinc-OH |

In another embodiment, the peptide of the invention comprises the general sequence twfX/xfin (Formula VI), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKctwfafinc, RRKKctwfcfinc, RRKKctwfdfinc, RRKKctwfefinc, RRKKctwfffinc, RRKKctwfGfinc, RRKKctwfhfinc, RRKKctwfifinc, RRKKctwfkfinc, RRKKctwflfinc, RRKKctwfmfinc, RRKKctwfnfinc, RRKKctwfpfinc, RRKKctwfqfinc, RRKKctwfrfinc, RRKKctwfsfinc, RRKKctwftfinc, RRKKctwfvfinc, RRKKctwfwfinc, and RRKKctwfyfinc. Also within the scope of the invention are peptides as shown above wherein the solubility tag is in the D form (rrkk). Also within the scope of the invention are functional derivatives of these peptides which are without any cyclization.

TABLE 3

Illustrative peptides.

| FPT ID | Sequence |
| --- | --- |
| PSP IV A1 | H-RRKKctwfafinc-OH |
| PSP IV A2 | H-RRKKctwfcfinc-OH |
| PSP IV A3 | H-RRKKctwfdfinc-OH |
| PSP IV A4 | H-RRKKctwfefinc-OH |
| PSP IV A5 | H-RRKKctwfffinc-OH |
| PSP IV A6 | H-RRKKctwfGfinc-OH |
| PSP IV A7 | H-RRKKctwfhfinc-OH |
| PSP IV A8 | H-RRKKctwfifinc-OH |
| PSP IV A9 | H-RRKKctwfkfinc-OH |
| PSP IV A10 | H-RRKKctwflfinc-OH |
| PSP IV A11 | H-RRKKctwfmfinc-OH |
| PSP IV A12 | H-RRKKctwfnfinc-OH |
| PSP IV A13 | H-RRKKctwfpfinc-OH |
| PSP IV A14 | H-RRKKctwfqfinc-OH |
| PSP IV A15 | H-RRKKctwfrfinc-OH |
| PSP IV A16 | H-RRKKctwfsfinc-OH |
| PSP IV A17-L | H-twftfin-OH |
| PSP IV A17-LS | H-RRKKtwftfin-OH |
| PSP IV A17-C | H-ctwftfinc-OH |
| PSP IV A17 | H-RRKKctwftfinc-OH |
| PSP IV A18 | H-RRKKctwfvfinc-OH |
| PSP IV A19 | H-RRKKctwfwfinc-OH |
| PSP IV A20 | H-RRKKctwfyfinc-OH |

In another embodiment, the peptide of the invention comprises the general sequence X/xwftfin (Formula VII), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from RRKKcawftfinc, RRKKccwftfinc, RRKKcdwftfinc, RRKKcewftfinc, RRKKcfwftfinc, RRKKcGwftfinc, RRKKchwftfinc, RRKKciwftfinc, RRKKckwftfinc, RRKKclwftfinc, RRKKcmwftfinc, RRKKcnwftfinc, RRKKcpwftfinc, RRKKcqwftfinc, RRKKcrwftfinc, RRKKcswftfinc, RRKKctwftfinc, RRKKcvwftfinc, RRKKcwwftfinc and RRKKcywftfinc. Also within the scope of the invention are peptides as shown above wherein the solubility tag is in the D form (rrkk). Also within the scope of the invention are functional derivatives of these peptides which are without any cyclization.

TABLE 4

Illustrative peptides.

| FPT ID | Sequence |
|---|---|
| PSP V A1 | H-RRKKcawftfinc-OH |
| PSP V A2 | H-RRKKccwftfinc-OH |
| PSP V A3 | H-RRKKcdwftfinc-OH |
| PSP V A4 | H-RRKKcewftfinc-OH |
| PSP V A5 | H-RRKKcfwftfinc-OH |
| PSP V A6 | H-RRKKcGwftfinc-OH |
| PSP V A7 | H-RRKKchwftfinc-OH |
| PSP V A8 | H-RRKKciwftfinc-OH |
| PSP V A9 | H-RRKKckwftfinc-OH |
| PSP V A10 | H-RRKKclwftfinc-OH |
| PSP V A11 | H-RRKKcmwftfinc-OH |
| PSP V A12 | H-RRKKcnwftfinc-OH |
| PSP V A13 | H-RRKKcpwftfinc-OH |
| PSP V A14 | H-RRKKcqwftfinc-OH |
| PSP V A15 | H-RRKKcrwftfinc-OH |
| PSP V A16 | H-RRKKcswftfinc-OH |
| PSP V A17 | H-RRKKctwftfinc-OH |
| PSP V A18 | H-RRKKcvwftfinc-OH |
| PSP V A19-C | H-cwwftfinc-OH |
| PSP V A19 | H-RRKKcwwftfinc-OH |
| PSP V A20 | H-RRKKcywftfinc-OH |

In another embodiment, the peptide of the invention comprises the general sequence wwftfiX/x (Formula VIII), where X/x is a, c, d, e, f, G, h, i, k, l, m, p, q, r, s, t, v, w, or y. The peptide may comprise a cysteine residue at the N and C terminal end for cyclisation and/or a solubility tag. In another embodiment, the peptide is selected from RRKKcwwftfiac, RRKKcwwftficc, RRKKcwwftfidc, RRKKcwwftfiec, RRKKcwwftfifc, RRKKcwwftfiGc, RRKKcwwftfihc, RRKKcwwftfiic, RRKKcwwftfikc, RRKKcwwftfilc, RRKKcwwftfimc, RRKKcwwftfipc, RRKKcwwftfiqc, RRKKcwwftfirc, RRKKcwwftfisc, RRKKcwwftfitc, RRKKcwwftfivc, RRKKcwwftfiwc, RRKKcwwftfiyc. Also within the scope of the invention are peptides as shown above wherein the solubility tag is in the D form (rrkk). Also within the scope of the invention are functional derivatives of these peptides which are without any cyclization.

TABLE 5

Illustrative peptides.

| FPT ID | Sequence |
|---|---|
| PSP VI A1 | H-RRKKcwwftfiac-OH |
| PSP VI A2 | H-RRKKcwwftficc-OH |
| PSP VI A3 | H-RRKKcwwftfidc-OH |
| PSP VI A4 | H-RRKKcwwftfiec-OH |

TABLE 5-continued

Illustrative peptides.

| FPT ID | Sequence |
|---|---|
| PSP VI A5 | H-RRKKcwwftfifc-OH |
| PSP VI A6 | H-RRKKcwwftfiGc-OH |
| PSP VI A7 | H-RRKKcwwftfihc-OH |
| PSP VI A8 | H-RRKKcwwftfiic-OH |
| PSP VI A9 | H-RRKKcwwftfikc-OH |
| PSP VI A10 | H-RRKKcwwftfilc-OH |
| PSP VI A11 | H-RRKKcwwftfimc-OH |
| PSP VI A13 | H-RRKKcwwftfipc-OH |
| PSP VI A14 | H-RRKKcwwftfiqc-OH |
| PSP VI A15 | H-RRKKcwwftfirc-OH |
| PSP VI A16 | H-RRKKcwwftfisc-OH |
| PSP VI A17 | H-RRKKcwwftfitc-OH |
| PSP VI A18 | H-RRKKcwwftfivc-OH |
| PSP VI A19 | H-RRKKcwwftfiwc-OH |
| PSP VI A20 | H-RRKKcwwftfiyc-OH |

In another embodiment, the peptide of the invention comprises the general sequence tksrfX/xn (Formula I), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from ctksrfanc, ctksrfcnc, ctksrfdnc, ctksrfenc, ctksrffnc, ctksrfGnc, ctksrfhnc, ctksrfinc, ctksrfknc, ctksrflnc, ctksrfmnc, ctksrfnnc, ctksrfpnc, ctksrfqnc, ctksrfrnc, ctksrfsnc, ctksrftnc, ctksrfvnc, ctksrfwnc and ctksrfync. Also within the scope of the invention are peptides as shown above wherein the solubility tag is in the L form (RRKK) or D form (rrkk). Also within the scope of the invention are functional derivatives of these peptides which are without any cyclization.

TABLE 6

Illustrative peptides.

| FPT ID | Sequence |
|---|---|
| PSP 1 | H-ctksrfanc-OH |
| PSP 2 | H-ctksrfcnc-OH |
| PSP 3 (P1-RI-CD) | H-ctksrfdnc-OH |
| PSP 4 | H-ctksrfenc-OH |
| PSP 5 | H-ctksrffnc-OH |
| PSP 6 | H-ctksrfGnc-OH |
| PSP 7 | H-ctksrfhnc-OH |
| PSP 8 | H-ctksrfinc-OH |
| PSP 9 | H-ctksrfknc-OH |
| PSP 10 | H-ctksrflnc-OH |
| PSP 11 | H-ctksrfmnc-OH |
| PSP 12 | H-ctksrfnnc-OH |
| PSP 13 | H-ctksrfpnc-OH |
| PSP 14 | H-ctksrfqnc-OH |
| PSP 15 | H-ctksrfrnc-OH |
| PSP 16 | H-ctksrfsnc-OH |
| PSP 17 | H-ctksrftnc-OH |
| PSP 18 | H-ctksrfvnc-OH |
| PSP 19 | H-ctksrfwnc-OH |
| PSP 20 | H-ctksrfync-OH |

In another embodiment, the peptide of the invention comprises the general sequence tX/xsrfin (Formula II), where X/x is a, c, d, e, f, G, h, i, k, l, m, n, p, q, r, s, t, v, w, or y. The peptide may comprise a cysteine residue at the N and C terminal end for cyclisation and/or a solubility tag. In another embodiment, the peptide is selected from rrkkctasrfinc, rrkkctcsrfinc, rrkkctdsrfinc, rrkkctesrfinc, rrkkctfsrfinc, rrkkaGsrfinc, rrkkcthsrfinc, rrkkctisrfinc, rrkkctksrfinc, rrkkctlsrfinc, rrkkctmsrfinc, rrkkctnsrfinc, rrkkctpsrfinc, rrkkctqsrfinc, rrkkctrsrfinc, rrkkctssrfinc, rrkkcttsrfinc, rrkkctvsrfinc, rrkkctwsrfinc and rrkkctysrfinc. Also within the scope of the invention are peptides as shown above wherein the solubility tag is in the L form (RRKK). Also within the scope of the invention are functional derivatives of these peptides which are without any cyclization.

TABLE 7

Illustrative peptides.

| FPT ID | Sequence |
| --- | --- |
| PSP II A1 | H-rrkkctasrfinc-OH |
| PSP II A2 | H-rrkkctcsrfinc-OH |
| PSP II A3 | H-rrkkctdsrfinc-OH |
| PSP II A4 | H-rrkkctesrfinc-OH |
| PSP II A5 | H-rrkkctfsrfinc-OH |
| PSP II A6 | H-rrkkctGsrfinc-OH |
| PSP II A7 | H-rrkkcthsrfinc-OH |
| PSP II A8 | H-rrkkctisrfinc-OH |
| PSP II A9 | H-rrkkctksrfinc-OH |
| PSP II A10 | H-rrkkctlsrfinc-OH |
| PSP II A11 | H-rrkkctmsrfinc-OH |
| PSP II A12 | H-rrkkctnsrfinc-OH |
| PSP II A13 | H-rrkkctpsrfinc-OH |
| PSP II A14 | H-rrkkctqsrfinc-OH |
| PSP II A15 | H-rrkkctrsrfinc-OH |
| PSP II A16 | H-rrkkctssrfinc-OH |
| PSP II A17 | H-rrkkcttsrfinc-OH |
| PSP II A18 | H-rrkkctvsrfinc-OH |
| PSP II A19 | H-rrkkctwsrfinc-OH |
| PSP II A20 | H-rrkkctysrfinc-OH |
| RRKK-PSP II A19 | H-RRKKctwsrfinc-OH |

In another embodiment, the peptide of the invention comprises the general sequence wwftX/xia (Formula IX), where X/x is a, c, d, e, G, h, i, k, l, m, n, p, q, r, s, v, w, or y. The peptide may comprise a cysteine residue at the N and C terminal end for cyclisation and/or a solubility tag. In another embodiment, the peptide is selected from RRKKcwwftaiac, RRKKcwwftciac, RRKKcwwftdiac, RRKKcwwfteiac, RRKKcwwftGiac, RRKKcwwfthiac, RRKKcwwftiiac, RRKKcwwftkiac, RRKKcwwftliac, RRKKcwwftmiac, RRKKcwwftniac, RRKKcwwftpiac, RRKKcwwftqiac, RRKKcwwftriac, RRKKcwwftsiac, RRKKcwwftviac, RRKKcwwftwiac, and RRKKcwwftyiac. Also within the scope of the invention are peptides as shown above wherein the solubility tag is in the D form (rrkk). Also within the scope of the invention are functional derivatives of these peptides which are without any cyclization.

TABLE 8

Illustrative peptides.

| Peptide ID | Sequence |
| --- | --- |
| PSP VII A1 | H-RRKKcwwftaiac-OH |
| PSP VII A2 | H-RRKKcwwftciac-OH |
| PSP VII A3 | H-RRKKcwwftdiac-OH |
| PSP VII A4 | H-RRKKcwwfteiac-OH |
| PSP VII A5 | H-RRKKcwwftGiac-OH |
| PSP VII A7 | H-RRKKcwwfthiac-OH |
| PSP VII A8 | H-RRKKcwwftiiac-OH |
| PSP VII A9 | H-RRKKcwwftkiac-OH |
| PSP VII A10 | H-RRKKcwwftliac-OH |
| PSP VII A11 | H-RRKKcwwftmiac-OH |
| PSP VII A 12 | H-RRKKcwwftniac-OH |
| PSP VII A 13 | H-RRKKcwwftpiac-OH |
| PSP VII A 14 | H-RRKKcwwftqiac-OH |
| PSP VII A 15 | H-RRKKcwwftriac-OH |
| PSP VII A 16 | H-RRKKcwwftsiac-OH |
| PSP VII A 17 | H-RRKKcwwfttiac-OH |
| PSP VII A 18 | H-RRKKcwwftviac-OH |

TABLE 8-continued

Illustrative peptides.

| Peptide ID | Sequence |
| --- | --- |
| PSP VII A 19 | H-RRKKcwwftwiac-OH |
| PSP VII A 20 | H-RRKKcwwftyiac-OH |

In another embodiment, peptides described herein have antiviral activity against at least one, preferably more than one virus that infects humans. In another embodiment, the peptides described herein have antiviral activity against more than one subtype of a virus, preferably subtypes that infects humans. For example, infection caused by various subtypes of HIV, RSV, HSV and CMV, including but not limited to RSV A2, HSV-2, CMV AD 169, HIV-1 92UG029, and the like, may be treated using peptides described herein. In another embodiment, the virus in not an influenza virus or an orthomyxovirus.

The featured peptides and biologically active variants thereof can be modified in numerous ways. For example, agents, including additional amino acid residues, other substituents, and protecting groups can be added to the amino terminus, the carboxy terminus, or both. For example, as described above, the peptides can be modified to include cysteine residues or other sulfur containing residues or agents that can participate in disulfide bond formation.

The peptides of the invention may also comprise one or more modified amino acids at any position(s) and/or N-terminal and/or C-terminal end to increase the solubility, stability, reactivity or improve other properties. These modifications include the addition of chemical groups such as but not limited to acetyl, carbobenzoyl, dansyl, a t-butyloxycarbonyl group, a 9-fluorenylmethyoxycarbonyl group or a hydrophilic groups to the amino-terminal end and/or t-buyloxycarbonyl, or an amido group or a para-nitrobenzyl ester group or a hydrophilic group to the carboxy-terminal end. They may also comprise modified amide bonds such as N-methylation.

In another embodiment, any of the peptides described herein include one or more substituents. For example, the peptide can include a substituent at the amino terminus, carboxy-terminus, and/or on a reactive amino acid residue side-chain. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group. The substituent can be a non-protein polymer, for example, a polyether, a polyethylene glycol (PEG), a polypropylene glycol, or a polyoxyalkylene, a polyalkylene glycol (for example, polypropylene glycol (PPG), a polybuylene glycol (PBG), or a PPG-PEG block/random polymer).

The non-protein polymer can vary in size and shape. For example, any of the non-protein polymers listed above (e.g., PEG) can be linear, branched, or comb-shaped. Regarding size, the molecular weight can vary. For example, the PEG can have a molecular weight of, for example, about 300 Da, about 1000 Da, about 2000 Da, about 3000 Da, about 4000 Da, about 5000 Da, about 6000 Da, about 7000 Da, about 8000 Da, about 9000 Da, about 10000 Da, about 11,000 Da, about 12000 Da about 13000 Da about 14000 Da about 15000 Da, about 20000 Da, about 30000 Da, about 40000 Da, or about 50000 Da. For example, the PEG can be of a molecular weight anywhere in between 300 DA and 2000 Da, 300 Da and 3000 Da, 1000 Da and 2000 Da and 1000 and 3000 Da. The non-protein polymer (e.g., PEG) can be linked to the peptide by any number of functional group chemistries (e.g., carboxylated-mPEGs, p-nitrophenyl-PEGs, aldehyde-PEGs, amino-PEGs, thiol-PEGs, maleimide-PEGs, aminoxy-PEGs, hydrazine-PEGs, tosyl-PEGs, iodoacetamide-PEGs, succiminidylsuccinate-PEGs, succinimidylglutarate-PEGS, succinimidylcarboxypentyl-PEGs, p-nitrophenyl carb onate-PEGs, or ethanethiol-PEGs). The non-protein polymer (e.g., PEG) can be linked to the peptide through any number of chemical groups including, but not limited to, amino-terminal amino acids, carboxy-terminal amino acids, free amines, and free sulfhydryl groups.

The non-protein polymer (e.g., PEG) may be a functionalized (for example, a monofunctional activated linear PEG, a homobifunctional activated linear PEG, a heterobifunctional activated linear PEG, a multiarmed activated PEG (e.g. 2-armed, 4-armed, 8-armed, etc.), a branched activated PEG and a comb-shaped activated PEG).

The anti-viral peptides of the invention may also comprise a reactive tag at their terminal amino acids for the purpose of detection, isolation, purification etc. These tags may include (but are not limited to) biotin, histidine, GST etc. Suitable tags are known in the art.

The peptides of the invention may also be linked with lipids (phospholipids) or Poly Ethylene Glycol to enhance/alter the solubility, proteolytic stability or other properties and or activity. Therefore, the peptides of the invention include such lipopeptides.

As used herein, the antiviral peptides of the invention may include a mimetic or peptidomimetic derivative which is a compound capable of mimicking the core structure of a peptide. Similarly, it is to be understood that the antiviral peptides may include one or more amino acid replacements, such as isosteres or bioisosteres.

In another embodiment, the antiviral peptides of the invention may be in multimeric form. The multimer could be a dimer, trimer or a tetramer; preferably a dimer. The monomeric antiviral peptides forming the multimer may be made up of the same or different peptides. In preferred embodiments, the peptides forming the multimer are covalently linked.

In another embodiment, the antiviral peptides of the invention may be presented in different physical forms. The physical form could be crystalline, amorphous or other which are well known in the art.

Various examples provided in this patent application demonstrate that the FPTs with substituted amino acids retain the antiviral activity as shown in various sequences described in Tables 1-8. Such derivatives are within the scope of this invention. In another embodiment, the amino acids of the antiviral peptides of the present invention may be substituted with conservative substitutions. Conservative substitution refers to replacement of amino acids with alternative amino acids which may alter the primary sequence but not the function. Examples of conservative amino acid substitutions include: valine, isoleucine and leucine; lysine and arginine; asparagine and glutamine; serine and threonine; glycine and alanine; phenylalanine and tyrosine and aspartic acid and glutamic acid. An amino acid within a given group may be conservatively substituted with another amino acid from the same group.

In another embodiment, the amino acids of the antiviral peptides of the present invention may be replaced with non-natural or unnatural amino acids and their derivatives including, but not limited to, β-amino acids (β3 and β2), Homo-amino acids, Proline and Pyruvic acid derivatives, 3-substituted Alanine derivatives, Glycine derivatives, Ring-substituted Phenylalanine and Tyrosine Derivatives, N-methyl amino acids and others which are well known in the art.

Peptides of the invention or derivatives thereof can be tested for their anti-viral activity using the methods as explained in the following Examples.

The disclosed peptides and their derivatives can be synthesized via any common methods used in peptide synthesis such as liquid phase or solid phase synthesis or any other methods well known in the art.

The peptides of the invention exhibit broad spectrum antiviral activity against viruses including various types and/or subtypes. The virus may be of human or animal origin, for example of simian origin. The preferred viruses are of human origin or human-infective viruses.

Thus, according to another aspect of the invention, one or more peptide of the invention as described above may be formulated into a pharmaceutical composition. This composition may include at least one peptide of the invention together with one or more pharmaceutically acceptable carriers, including excipients, such as diluents, carriers and the like, and additives, such as stabilizing agents, preservatives, solubilizing agents, buffers and the like, as may be desired. A pharmaceutically acceptable carrier is a compound with which a peptide of the present invention may be administered and which contains one or more non-toxic ingredients which do not inhibit or reduce the effectiveness of the active antiviral peptide described herein.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, for example, inhalatory administration.

Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In another embodiment, when administered to an animal, the peptide of the present invention or compositions and pharmaceutically acceptable carriers are sterile. Water is a preferred carrier when the peptides of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

In another embodiment, specific non-limiting examples of carriers and excipients include but are not limited to water, saline, dextrose, glycerol, ethanol, or the like or combinations thereof. Formulation excipients may include polyvinylpyrrolidone, gelatin, hydroxyl cellulose, acacia, polyethylene glycol, mannitol, sodium chloride or sodium citrate.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

For topical administration formulations, any of a variety of creams, ointments, gels, lotions and the like may be employed.

When intended for oral administration, the composition is preferably in solid or liquid form, where semi-solid, semi-liquid, suspension and gel forms are included within the forms considered herein as either solid or liquid.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included. Water containing at least one or more buffering constituents is preferred along with or without stabilizing agents, preservatives and solubilizing agents. When the composition is in the form of a capsule (e.g. a gelatin capsule), it can contain, in addition to materials of the above type, a liquid carrier such as polyethylene glycol, cyclodextrin or a fatty oil.

For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

It is to be understood that any suitable route of administration or delivery method may be used with the peptides described herein, including but not limited to oral, parenteral, depot, buccal, and the like.

In certain embodiments the peptide(s) are formulated with a non-covalent carrier. Non-covalent carriers are well known to those of skill in the art.

In certain embodiments, the peptide(s) are complexed with carriers such as lipids or formulated in liposomes, biodegradable or non-biodegradable microparticles, microcapsules, microspheres and nanoparticles. Methods of producing liposomes, microparticles, microcapsules, microspheres and nanoparticles and complexing or encapsulating compounds therein are well known to those of skill in the art.

In certain embodiments the antiviral peptide(s) described herein are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm.

Illustrative oil in water (O/W) and/or water in oil (W/O) nanoemulsions include, but are not limited to:

1) Surfactant micelles—micelles composed of small molecules surfactants or detergents (e.g., SDS/PBS/2-propanol) which are suitable for predominantly hydrophobic peptides;

2) Polymer micelles—micelles composed of polymer, copolymer, or block copolymer surfactants (e.g., Pluronic L64/PBS/2-propanol) which are suitable for predominantly hydrophobic peptides;

3) Blended micelles: micelles in which there is more than one surfactant component or in which one of the liquid phases (generally an alcohol or fatty acid compound) participates in the formation of the micelle (e.g., Octanoic acid/PBS/EtOH) which are suitable for predominantly hydrophobic peptides;

4) Integral peptide micelles–blended micelles in which the peptide serves as an auxiliary surfactant, forming an integral part of the micelle (e.g., amphipathic peptide/PBS/mineral oil) which are suitable for amphipathic peptides; and 5) Pickering (solid phase) emulsions–emulsions in which the peptides are associated with the exterior of a solid nanoparticle (e.g., polystyrene nanoparticles/PBS/no oil phase) which are suitable for amphipathic peptides.

In another embodiment, the invention relates to a peptide or composition of the invention for use as a medicament.

Administration of the peptides and compositions of the present invention include without limitation oral, topical, parenteral, sublingual, rectal, vaginal, ocular, pulmonary (inhalation) and intranasal. Parenteral administration includes subcutaneous injections, intravenous, intramuscular, intrasternal injection or infusion techniques. Preferably, the compositions are administered parenterally, pulmonary or orally. Pharmaceutical compositions of the invention can be formulated so as to allow a peptide of the present invention to be bioavailable upon administration of the composition to an animal, preferably human. Compositions can take the form of one or more dosage units, where for example, a tablet can be a single dosage unit, and a container comprising a peptide of the present invention in aerosol form can hold a plurality of dosage units.

Parenteral administration includes, but is not limited to, intradermal, intramuscular, intraperitoneal, intravenous, subcutaneous, intranasal, epidural, intracerebral, intraventricular, intrathecal, intravaginal or transdermal. The preferred mode of administration is left to the discretion of the practitioner, and will depend in part upon the site of the medical condition.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The peptides or compositions are administered in a therapeutically effective amount. The terms "therapeutically effective amount" or "pharmaceutically effective amount"

refer to the amount and/or dosage, and/or dosage regime of one or more compounds necessary to bring about the desired result e.g., an amount sufficient to reduce or block propagation of a virus, or an amount sufficient to lessen the severity or delay the progression of a symptoms of the viral disease (e.g., therapeutically effective amounts), an amount sufficient to reduce the risk or delaying the onset, and/or reduce the ultimate severity of a disease caused by a viral infection (e.g., prophylactically effective amounts).

The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a peptide of the present invention by weight of the composition. When intended for oral administration, this amount can be varied to range from about 0.1% to about 80% by weight of the composition. Preferred oral compositions can comprise from about 4% to about 50% of the peptide of the present invention by weight of the composition.

Preferred compositions of the present invention are prepared so that a parenteral dosage unit contains from about 0.01% to about 2% or more by weight of the peptide of the present invention.

For intravenous administration, the composition can comprise from about typically about 0.1 mg/day to about 250 mg/day, preferably, between about 0.1 mg/day and about 50 mg/day.

The peptide may be administered therapeutically or prophylactically. Suitable treatment is given 1-4 times daily and preferably continued for 1-7 days or more. The terms "treatment", "treating", or "treat" as used herein, refer to actions that produce a desirable effect on the symptoms or pathology of a disease or condition, particularly those that can be effected utilizing the peptides described herein, and may include, but are not limited to, even minimal changes or improvements in one or more measurable markers of the disease or condition being treated. Treatment also refers to delaying the onset of, retarding or reversing the progress of, reducing the severity of, or alleviating or preventing either the disease or condition to which the term applies, or one or more symptoms of such disease or condition. "Treatment", "treating", or "treat" does not necessarily indicate complete eradication or cure of the disease or condition, or associated symptoms thereof. In another embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The peptides or compositions of the present invention can be administered by any convenient route, for example by infusion or bolus injection, by absorption through epithelial or mucocutaneous linings.

Pulmonary administration can also be employed, e.g. by use of an inhaler or nebulizer, and formulation with an aerosolizing agent, or via perfusion in a fluorocarbon or synthetic pulmonary surfactant. In certain embodiments, the peptide of the present invention or compositions can be formulated as a suppository, with traditional binders and carriers such as triglycerides.

As explained above, depending on the route of administration, the anti-viral peptides of the invention may be formulated by any means known in the art, including but not limited to tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art.

Administration may also be together with another active compound, for example another antiviral compound. More than one peptide of the invention may also be administered.

Peptides described herein can also be provided as pharmaceutically acceptable salts. A "pharmaceutically acceptable salt" includes a salt with an inorganic base (for example, alkali metals such as sodium or potassium; alkaline earth metals such as calcium and magnesium or aluminium; and ammonia), organic base (for example, trimethylamine, triethylamine, pyridine, picoline, ethanolamine, diethanolamine, and triethanolamine), inorganic acid (for example, hydrochloric acid, hydroboric acid, nitric acid, sulfuric acid, and phosphoric acid) or organic acid (for example, formic acid, acetic acid, Trifluoroacetic acid, fumaric acid, oxalic acid, tartaric acid, maleic acid, citric acid, succinic acid, malic acid, methanesulfonic acid, benzenesulfonic acid and p-toluenesulfonic acid). The examples cited herein are non-limiting.

The invention also relates to a kit comprising a peptide or composition of the invention and instructions for use and optionally adjuvants.

The invention also relates to a screening method for detecting a peptide that has antiviral activity comprising making a derivative of an isolated anti-viral peptide described herein, exposing the peptide to the virus and screening for antiviral activity.

The invention also relates to an isolated nucleic acid molecule, including a DNA or RNA molecule, encoding an anti-viral peptide of the invention. In another embodiment, the isolated nucleic acid is not naturally occurring.

The invention also relates to a vector comprising a nucleic acid encoding an anti-viral peptide of the invention. The vector may be an expression vector, especially for expression in eukaryotic cells. Such vectors can, for example, be viral, plasmid, cosmid, or artificial chromosome (e.g., yeast artificial chromosome) vectors.

The vectors described herein can be introduced into cells or tissues by any one of a variety of known methods within the art. Such methods are described for example in Sambrook et al., Molecular Cloning: A Laboratory Manual, Cold Spring Harbor, 4th edition (Jun. 15, 2012).

The invention also relates to a host cell comprising an anti-viral peptide of the invention.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known in the art.

Thus, in the present invention, cells can be transfected in vitro or ex vivo, and the expressed peptide can be isolated therefrom by methods known in the art. The cells can also be administered to a subject or, alternatively, cells can be directly modified in vivo.

The invention also relates to a combination comprising an anti-viral peptide of the invention and a second agent selected, for example selected from a nucleic acid, peptide, protein, contrast agent, antibody, toxin and small molecule.

The invention also relates to a recombinant library, for example a phage library, comprising a peptide of the invention.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure. The specifics of these examples should not be treated as limiting.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

EXAMPLES

The following non-limiting examples are provided to further illustrate the present invention.

Example 1

Materials and Methods

Cell culture and virus: HSV, RSV, CMV and HIVs were propagated by multiple passaging in the Vero, Hep-2, HFFF-2 cells and PBMCs respectively to obtain high titre working stocks.

Peptide synthesis: Peptides were synthesized by Mimotopes (Australia) or Genscript (USA) using a solid state method. The sequences of illustrative peptides used in the study are listed in Tables 1-8. All the peptides were purified by HPLC (with more than >90 purity) and the sequences were confirmed by Mass spectrometer analysis. The sequence "RRKK" (or "rrkk") is optionally added to the N terminal end of all peptides to increase the solubility. All the peptides are synthesized using dextro-amino acids or levo-amino acids, depending upon the sequence. All the peptides were cyclised with disulphide bond using the cysteine residues present in the peptide.

Cytopathic effect (CPE) assay for HSV, RSV and CMV: Appropriate cells were seeded into 96 well plates and incubated overnight until they reached ~70% confluency. Viruses were treated with various concentrations of peptide or vehicle for 90 minutes at 4° C. and added on to the confluent monolayer of cells for the rest of the assay. At the end of the incubation period, the viability of the cells was determined by adding MTT reagent and incubating the plates at 37° C. for 2-4 hours at 5% $CO_2$. After the incubation, 100% isopropanol was added to solubilise the formazan crystals and the absorbance was recorded at 540 nm subtracting the background at 620 nm.

Pauwels formula (shown below) was used to calculate the percent cell protection achieved by the positive control or test compounds.

Percent cell protection=([ODt]virus−[ODc]virus/[ODc]mock−[ODc]virus)×100 where:

[ODt]virus=the optical density measured in a well examining the effect of a given concentration of test article or positive control on virus-infected cells.

[ODc]virus=the optical density measured in a well examining the effect of the negative control on virus-infected cells.

[ODc]mock=the optical density measured in a well examining the effect of the negative control on mock-infected cells.

These percentages were used to determine the $EC_{50}$ which were calculated by non-linear regression analysis with IDBS XLFit Excel Add-in Version 5.4.0.8

TABLE 9

CPE assay length and the multiplicity of infection (MOI)

| Virus | Assay length (days) | MOI |
|---|---|---|
| HSV | 4 | 0.02 |
| RSV | 5 | 0.02 |
| CMV | 14 | 0.006 |
| HIV-1 | 7 | 0.1 |

Anti-HIV Efficacy Evaluation in Fresh Human PBMCs: PBMCs were infected with various concentrations of peptide treated viruses and incubated at 37° C., 5% $CO_2$ for seven days. After this incubation, the cells were centrifuged down and the supernatants were collected for reverse transcriptase activity (RT) assay. The cytotoxic effects of the compounds were studied with the addition of MTS to the cells following the removal of the supernatant. Data analysis for $IC_{50}$ and $TC_{50}$ was done by the CRO with their in house computer program.

Reverse transcriptase activity assay: Reverse transcriptase (RT) assay was carried out in a microtiter plate. Briefly Tritiated thymidine triphosphate (3H-TTP, 80 Ci/mmol, NEN;(GE Healthcare) was prepared as a stock solution by combining 150 µL poly rA (20 mg/mL) with 0.5 mL oligo dT (20 units/mL) and 5.35 mL sterile dH2O. Fresh RT reaction buffer was prepared with 125 µL 1.0 M EGTA, 125 µL dH2O, 125 µL 20% Triton X100, 50 µL 1.0 M Tris (pH 7.4), 50 µL 1.0 M DTT, and 40 µL 1.0 M $MgCl_2$. The final reaction mixture was obtained by mixing 1 part of 3H-TTP, 4 parts $dH_2O$, 2.5 parts poly rA:oligo dT stock and 2.5 parts reaction buffer. Ten microliters of this reaction mixture was added to the microtiter plate and 15 µL of virus containing supernatant is added and mixed. Then the plate was incubated at 37° C. for 60 minutes. After the incubation, the reaction volume was spotted onto DE81 filter-mats (Wallac), washed extensively with 5% sodium phosphate buffer or 2× SSC (Life Technologies), then in distilled water which was followed by 70% ethanol wash and air drying. Standard liquid scintillation techniques were used to quantify the incorporated radioactivity (counts per minute, CPM).

Cytotoxicity Assay 1: At the end of the RT assay, 20 µL of soluble tetrazolium-based MTS (CellTiter 96 Reagent, Promega) reagent was added into each well of the plate to determine cell viability and quantify compound toxicity. The microtiter plates were then incubated at 37° C. for 4-6 hrs in a humidified, 5% $CO_2$ atmosphere. The incubation intervals were chosen based on empirically determined times for optimal dye reduction. The amount of soluble formazan produced by cellular reduction of MTS was measured spectrophotometrically at 490/650 nm with a micro-plate reader.

Cytotoxicity Assay 2: MDCK cells or A549 cells (~5000 cells/well) are grown overnight on 96 well plates. The media is replaced by serially diluted peptides and incubated again for 24/48 h. The culture medium is removed and 20 µl of CellTiter 96® AQueous One Solution [3-(4,5-dimethylthiozol-2-yl)-3,5-dipheryl tetrazolium bromide] (Promega, Wis., USA) is added and incubated at 37° C. for 2 h. The optical density is measured at 490 nm in an microplate reader (iMARK, BioRad, USA).

Alanine Scanning: Purified viruses are quantified by Bradford assay (Thermo Scientific, US). 15 µg/well of purified virus is coated onto 96-well ELISA microplate (eppendorf, US) overnight at 4° C. Coated wells are washed twice with 1×PBST (Phosphate buffered saline with Tween-20) and blocked with 5 mg/ml BSA in 1×PBS at room temperature for 1hr. The coated wells are incubated with 150 µM biotin conjugated peptides in 1% BSA (Bovine serum albumin)/1×PBST for 2 hr at room temperature. After three washes using 1×PBST, the biotin conjugated peptides are detected using primary anti-biotin rabbit (Cell Signaling 1:250, MA) and HRP conjugated anti-rabbit secondary antibodies (Abcam 1:5000, MA). The absorbance is read on Biorad iMark microplate reader at 415 nm.

Hemagglutination assay: Hemagglutination of chicken Red Blood Cells (cRBCs) are carried out in V-bottom 96 well microtiter plates as explained in Jones et al., Journal of Virology, 80 (24):11960-11967 (2006).

Bradford Assay: Protein quantification is done with Coomassie (Bradford) Protein assay kit (Thermo scientific, USA) as per manufacturer's instructions.

$IC_{50}$ Calculation: All experiments are done in triplicates and the data represents the results of at least three independent determinations. The $IC_{50}$ values are calculated based on dose-response curves as analyzed by Graphpad Prism™ software or IDBS XLFit Excell Add-in Version 5.4.0.8.

Hemolytic Assay: Freshly obtained human red blood cells are washed with PBS (pH 7.4) buffer for three times by centrifugation at 500×g for 10 minutes. Peptides are incubated with the wash RBCs in a V-bottom microtiter plate for 1 hour. 1% Triton X-100 is used as positive control. After the incubation, the plate is centrifuged at 500×g for 5 minutes and the supernatants are transferred to a fresh clear bottom 96 well plate and the absorbance of the is measured at 545 nm with iMark microplate reader (Biorad, USA).

Example 2

Effect of Anti-viral peptides on Hemagglutination activity: In this example, anti-viral peptides are tested for its ability to inhibit hemagglutination of viruses to support whether the peptides inhibit the virus replication by attaching to HA protein of the viruses. Briefly, 10 µM of peptide is mixed with 4HAU/50 µl virus and the HA activity is measured with chicken Red Blood Cells. No inhibition of hemagglutination activity was observed with the peptide treatment.

Example 3

Cytotoxic effects of FPTs on human hepatocytes: The cytotoxic effects of anti-viral peptides on human hepatic cell HepaRG™, a cell with a proven differentiated hepatocyte phenotype under the cell-culture conditions, are analyzed by AvantiCell Science Ltd, UK Briefly, cytotoxicity of the test materials is measured as the release of cytosolic contents, specifically cytosolic dehydrogenases, during a 24-hour challenge. Cell-content release into culture medium is measured by a sensitive fluorescence-based assay. Assay performance was monitored by the use of negative controls (test material solvents) and positive controls in the form of known cytotoxic agents. At the end of the challenge period, the assay readout is generated by a standard methodology, and results are calculated as percentage cell lysis (% lysis), by comparing test measurements with that generated by a fully-lysed detergent-treated control (100% lysis).

Example 4

Figure 12:
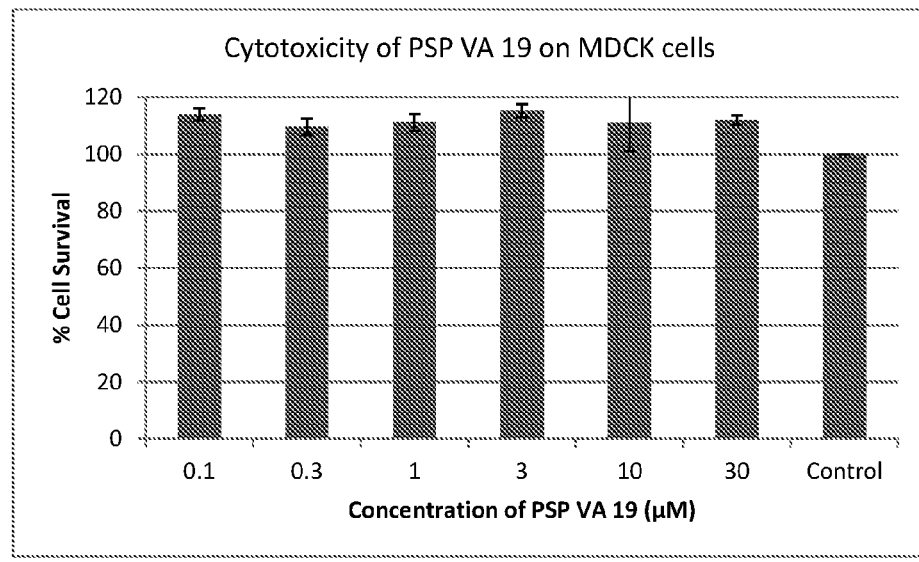
FIG. 12: Cytotoxic effects of anti-viral peptides PSP V A19 on MDCK and A549 cells. Cytotoxic effects of anti-viral peptide PSP V A19. The toxicity effects of the above peptide were tested at many different concentrations on MDCK and A549 cells as described in Example 4, and compared to untreated control. Data are presented as the mean value±standard deviation of triplicate measurements.
Figure 12:
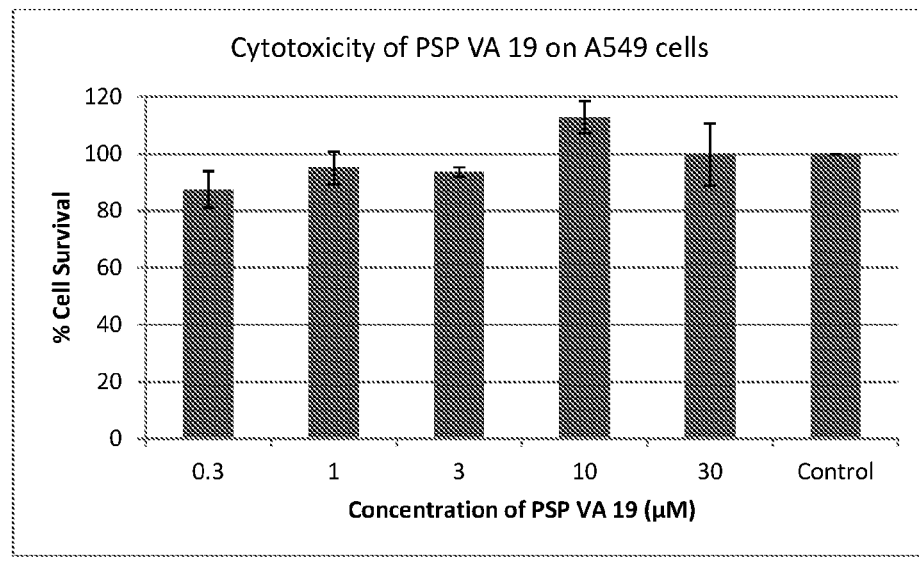
Figure 13:
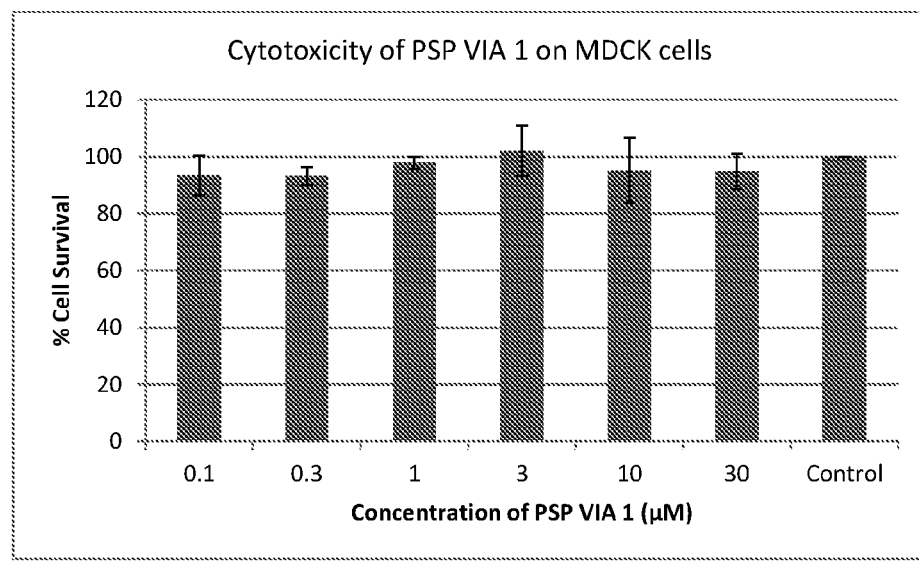
FIG. 13: Cytotoxic effects of anti-viral peptides PSP VI A1 on MDCK and A549 cells. Cytotoxic effects of anti-viral peptide PSP VI A1. The toxicity effects of the above peptide were tested at many different concentrations on MDCK and A549 cells as described in Example 4, and compared to untreated control. Data are presented as the mean value±standard deviation of triplicate measurements.
Figure 13:
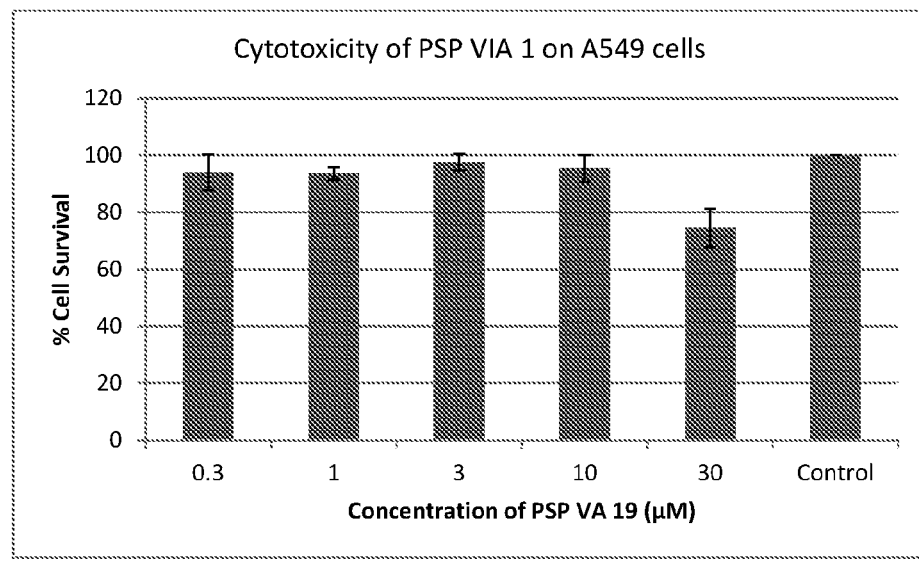

Cytotoxic effects of anti-viral peptides on MDCK cells or A549 cells: The cytotoxic effects of anti-viral peptides are shown in FIG. 12 and FIG. 13 which are assessed as explained in Example 1. Briefly, the MDCK cells/A549 cells are treated with either 0 µM peptide (Mock) or increasing concentrations (i.e., 0.1 µM, 0.3 µM, 1 µM, 3 µM, 10 µM, 30 µM and 100 µM) of PSP V A19 and PSP VI A1 and the cell death is determined by 48 hours post infection by a cytotoxicity assay with CellTiter 96® $AQ_{ueous}$ One Solution cell proliferation assay kit (Promega, USA) as explained by manufacturer. The results are normalized to the mock treated cells. As shown in the results, the PSP V A19 and PSP VI A1 showed no significant toxicity against MDCK cells/A549 cells with $CE_{50}$ (Cytotoxic Effect 50) value more than 30 µM.

Example 5

Figure 14:
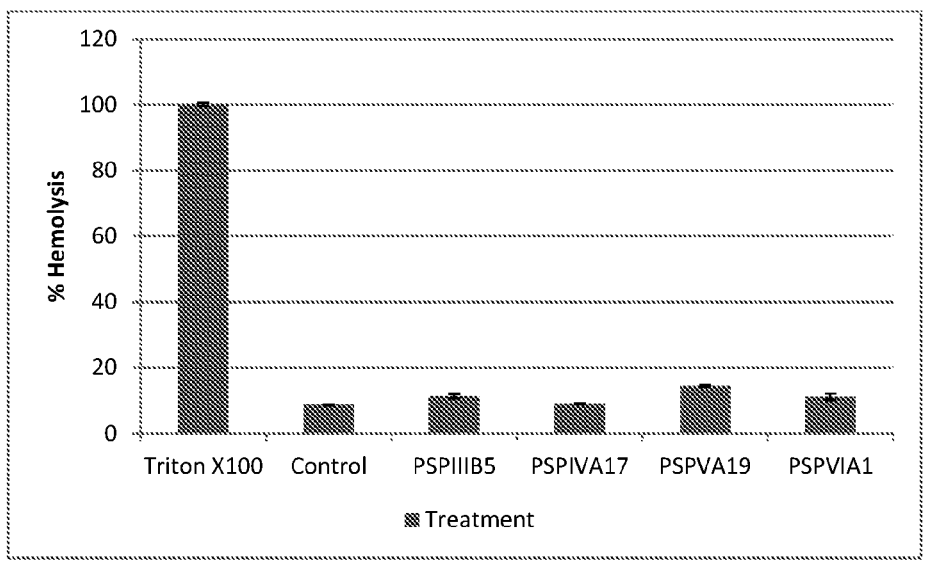
FIG. 14: Hemolytic activities of different antiviral peptides at 30 μM concentration. Hemolytic activities of Triton X-100 or different antiviral peptides PSP III B5, PSP IV A17, PSP V A19 and PSP VI A1 were tested at 30 μM concentration as described in Example 5, and compared to untreated control.

Hemolytic activities of FPTs: The hemolytic effects of the anti-viral peptides are shown in FIG. 14 which was assessed as explained in Example 1. Briefly, different concentrations of the peptides are incubated with human red blood cells and the hemolysis is determined at one hour post incubation by the absorbance of released hemoglobin in the supernatant at 545 nm with Biorad iMark microplate reader.

Example 6

The peptides in Table 10 show the $IC_{50}$ or $EC_{50}$ values for illustrative anti-viral peptides described herein against various matrix layer containing viruses.

TABLE 10

$IC_{50}$ or $EC_{50}$ values (µM) of illustrative peptides as assessed by in vitro methods described herein.

| Compound | RSV-A2 ($EC_{50}$) | HSV-2 ($EC_{50}$) | CMV AD169 ($EC_{50}$) | HIV-1 92UG029 ($IC_{50}$) |
|---|---|---|---|---|
| H-RRKKcwwftfiac-OH (PSP VI A1) | 17.8 | ~30 | 13.8 | 60.8 |
| H-RRKKctwftfinc-OH (PSP IV A17) | 12.6 | ~30 | 18.9 | — |
| H-RRKKtwftfin-OH (PSP IV A17-LS) | — | — | — | 79.1 |
| H-cwwftfinc-OH (PSP V A19-C) | — | — | — | 66.5 |

REFERENCES

1. Robert A Lamb GDP, ed Paramyxoviridae. 5 ed. Philadelphia: Lippincott Williams & Wilkins; 2007. David M Knipe P M H, ed. Fields Virology; No. 1.

2. Nair H, Nokes D J, Gessner B D, et al. Global burden of acute lower respiratory infections due to respiratory syncytial virus in young children: a systematic review and meta-analysis. *Lancet. May* 1, 2010; 375(9725):1545-1555.
3. Eric A. F. SimOes J P D, Michael Boeckh, Louis Bont, James E. Crowe Jr, Paul Griffiths, Frederick G. Hayden R L H, Rosalind L. Smyth, Keith Spencer, Steffen Thirstrup, Edward E. Walsh—Whitley a R J. Challenges and Opportunities in Developing Respiratory Syncytial Virus Therapeutics. *The Journal of Infectious Diseases.* 2015; 211 (S1): S1-20.
4. Edward S Mocarski J, Thomas Shenk, Robert F Pass, ed *Cytomegaloviruses.* Philadelphia: Lippincott Williams & Wilkins; 2007. David M Knipe P M H, ed. Fields Virology; No. 2.
5. Philip E Pellet B R, ed Herpesviridae. 5 ed. Philadelphia: Lippincott Williams & Wilkins; 2007. David M Knipe PMH, ed. Fields Virology; No. 2.
6. Plosa E J, Esbenshade J C, Fuller M P, Weitkamp J H. Cytomegalovirus infection. *Pediatr Rev. April* 2012; 33(4):156-163; quiz 163.
7. Rawlinson W D, Boppana S B, Fowler K B, et al. Congenital cytomegalovirus infection in pregnancy and the neonate: consensus recommendations for prevention, diagnosis, and therapy. *Lancet Infect Dis. Mar.* 10, 2017.
8. Khalil A, Jones C, Ville Y. Congenital cytomegalovirus infection: management update. *Curr Opin Infect Dis. June* 2017; 30(3):274-280.
9. Tan B H. Cytomegalovirus Treatment. *Curr Treat Options Infect Dis.* 2014; 6(3):256-270.
10. Harter G, Michel D. Antiviral treatment of cytomegalovirus infection: an update. *Expert Opin Pharmacother. April* 2012; 13 (5): 623-627.
11. Bernard Roizman D M K, Richard J Whitley, ed *Herpes Simplex Viruses.* 5 ed. Philadelphia: Lippincott Williams & Wilkins; 2007. David M Knipe P M H, ed. Fields Virology; No. 2.
12. Harris M. Globally, an estimated two-thirds of the population under 50 are infected with herpes simplex virus type 1. Geneva: World Health Organization; 2015.
13. Looker K J, Magaret A S, May M T, et al. Global and Regional Estimates of Prevalent and Incident Herpes Simplex Virus Type 1 Infections in 2012. *PLoS One.* 2015; 10(10):e0140765.
14. Katharine J Looker G P G, George P Schmid. An estimate of the global prevalence and incidence of herpes simplex virus type 2 infection. *Bulletin of the World Health Organization* 2008; 86(10): 737-816.
15. Le Cleach L, Trinquart L, Do G, et al. Oral antiviral therapy for prevention of genital herpes outbreaks in immunocompetent and nonpregnant patients. *Cochrane Database Syst Rev. Aug.* 3, 2014(8):CD009036.
16. Vere Hodge R A F H. Antiviral agents for herpes simplex virus. *Advances in Pharmacology.* 2013; 67:1-38.
17. Goff S P, ed Retroviridae: *The Retroviruses and their replication.* 5 ed. Philadelphia: Lippincott Williams & Wilkins; 2007. David M Knipe P M H, ed. Fields Virology; No. 2.
18. Daniel R Kuritzkes B D W, ed HIV-1 *Pathogenesis, clinical manifestations and treatment.* 5 ed. Philadelphia: Lippincott Williams & Wilkins; 2007. David M Knipe P M H, ed. Fields Virology; No. 2.
19. Prokofjeva M M, Kochetkov S N, Prassolov V S. Therapy of HIV Infection: Current Approaches and Prospects. *Acta Naturae. October-December* 2016; 8(4):23-32.
20. Joseph L. Kukura M P T, ed *Current Challenges and Opportunities in the Pharmaceutical Industry*: John Wiley & Sons; 2010. Ende DJa, ed. Chemical Engineering in the Pharmaceutical Industry: R&D to Manufacturing; No. 1.
21. Fry D C. Targeting protein-protein interactions for drug discovery. *Methods Mol Biol.* 2015; 1278:93-106.
22. Scott D E, Bayly A R, Abell C, Skidmore J. Small molecules, big targets: drug discovery faces the protein-protein interaction challenge. *Nat Rev Drug Discov.* August 2016; 15(8):533-550.
23. Samaranayake H, Wirth T, Schenkwein D, Raty J K, Yla-Herttuala S. Challenges in monoclonal antibody-based therapies. *Ann Med.* 2009; 41(5):322-331.
24. Fosgerau K, Hoffmann T. Peptide therapeutics: current status and future directions. *Drug Discov Today. January* 2015; 20(1):122-128.
25. Otvos L, Jr., Wade J D. Current challenges in peptide-based drug discovery. *Front Chem.* 2014; 2:62.
26. Oyston P C, Fox M A, Richards S J, Clark G C. Novel peptide therapeutics for treatment of infections. *J Med Microbiol. August* 2009; 58(Pt 8):977-987.
27. Seo M D, Won H S, Kim J H, Mishig-Ochir T, Lee B J. Antimicrobial peptides for therapeutic applications: a review. *Molecules. Oct.* 18, 2012; 17(10): 12276-12286.
28. Rajik M, Jahanshiri F, Omar A R, Ideris A, Hassan S S, Yusoff K. Identification and characterisation of a novel anti-viral peptide against avian influenza virus H9N2. *Virol J. Jun.* 5, 2009; 6:74.
29. Rajik M, Yusoff K. Peptide inhibitors against influenza virus.*Antivir Chem Chemother. Mar.* 7, 2011; 21(4):151-154.
30. Vlieghe P, Lisowski V, Martinez J, Khrestchatisky M. Synthetic therapeutic peptides: science and market. *Drug Discov Today. January* 2010; 15(1-2):40-56.
31. Rajik M, Inventor; Viramatix Sdn Bhd, assignee. Broad-spectrum anti-influenza therapeutic peptides2015.
32. Rajik M, Inventor; Viramatix Sdn Bhd, assignee. Peptides and uses therefor as antiviral agents2016.

Each document and publication cited herein is incorporated herein by reference in its entirety.

What is claimed is:

1. A method for treating an existing infection in a host animal, where the infection is caused at least in part by a virus containing a matrix protein layer or an enveloped virus, the method comprising administering a therapeutically effective amount of a peptide comprising the sequence twftfin or an analog or derivative of twftfin of the formula A1-A2-A3-A4-A5-A6-A7, where A1 is t or w, A2 is k or w, A3 is s or f, A4 is r or t, A5 is f, h, i, n, or w, A6 is i or d, and A7 is n or a, and where any one or any two of A1, A2, A3, A4, A5, A6, or A7 is optionally replaced with another D-amino acid or L-amino acid, where the peptide has a length of about 50 residues or less, or a pharmaceutical composition of any of the foregoing; where the virus is not an influenza virus or an orthomyxovirus.

2. The method of claim 1 wherein the virus is a retrovirus, lentivirus, paramyxovirus, flavivirus, hepatitis C virus, tick borne encephalitis, yellow fever, dengue fever virus, filovirus, togavirus, bunyavirus, herpesvirus, hepadnavirus, negative-sense, single-stranded RNA virus, or coronavirus.

3. The method of claim 1 wherein the virus is HIV, Ebola, Marburg virus, rubella virus, hantavirus, arenavirus, cytomegalovirus, hepatitis B virus, or torovirus.

4. The method of claim 1 wherein the infection is AIDS, herpes, or SARS.

5. The method of claim 1 wherein any one of A1, A2, A3, A4, A5, A6, or A7 is optionally replaced with another D-amino acid or L-amino acid.

6. The method of claim 1 wherein any one or any two of A1, A2, A3, A4, A5, A6, or A7 is replaced with the corresponding L-amino acid.

7. The method of claim 1 wherein the peptide comprises the sequence twftfin, X/xwftfin, tX/xftfin, twX/xtfin, twfX/xfin, twftX/xin, twftfX/xn, twftfiX/x, or X/xwftfiX/x, where X/x is glycine, or any D-amino acid, or any L-amino acid, and where in each sequence one additional amino acid is inserted, deleted, or changed to a different D-amino acid, or to glycine, or to any L-amino acid.

8. The method of claim 1 wherein the peptide comprises the sequence twftfin, X/xwftfin, tX/xftfin, twX/xtfin, twfX/xfin, twftX/xin, twftfX/xn, twftfiX/x, or X/xwftfiX/x, where X/x is glycine, or any D-amino acid, or any L-amino acid.

9. The method of claim 8 wherein the peptide comprises the sequence twftfin, X/xwftfin, tX/xftfin, twX/xtfin, twfX/xfin, twftX/xin, twftfX/xn, or twftfiX/x.

10. The method of claim 8 wherein the peptide comprises the sequence X/xwftfiX/x.

11. The method of claim 1 wherein the peptide comprises the sequence H-RRKKctwftfinc-OH, H-RRKKcwwftfinc-OH, or H-RRKKcwwftfiac-OH.

12. The method of claim 1 wherein the peptide further comprises an N-terminal, a C-terminal cysteine residue, or both an N-terminal and a C-terminal cysteine residue.

13. The method of claim 1 wherein the peptide further comprising one or more solubility tags, each of which is independently selected.

14. The method of claim 1 wherein the peptide is in cyclic form.

15. The method of claim 1 wherein the peptide has an $IC_{50}$ against the virus of less than 100 μM.

16. The method of claim 1 wherein the peptide is included in a composition adapted for administration nasally, pulmonarilly, orally, or parenterally.

17. The method of claim 1 wherein the virus is a respiratory syncytial virus.

18. The method of claim 1 wherein the peptide is H-RRKKcwwftfiac-OH.

19. The method of claim 1 wherein the peptide is H-RRKKcwwftfinc-OH.

* * * * *